(12) United States Patent
Lee et al.

(10) Patent No.: US 11,903,912 B2
(45) Date of Patent: *Feb. 20, 2024

(54) COMPOSITION FOR PREVENTING AND TREATING BREAST CANCER INCLUDING SELENOPSAMMAPLIN A AS ACTIVE INGREDIENTS

(71) Applicant: Seoul National University R & DB Foundation, Seoul (KR)

(72) Inventors: Sang Kook Lee, Seoul (KR); Hyeung Geun Park, Seoul (KR); Woong Sub Byun, Seoul (KR); Hae Ju Han, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 506 days.

This patent is subject to a terminal disclaimer.

(21) Appl. No.: 16/981,916

(22) PCT Filed: Oct. 15, 2019

(86) PCT No.: PCT/KR2019/013461
§ 371 (c)(1),
(2) Date: Sep. 17, 2020

(87) PCT Pub. No.: WO2021/054510
PCT Pub. Date: Mar. 25, 2021

(65) Prior Publication Data
US 2021/0259997 A1    Aug. 26, 2021

(30) Foreign Application Priority Data

Sep. 20, 2019  (KR) ........................ 10-2019-0115722

(51) Int. Cl.
*A61K 31/165*   (2006.01)
*A61P 35/00*    (2006.01)

(52) U.S. Cl.
CPC ............ *A61K 31/165* (2013.01); *A61P 35/00* (2018.01)

(58) Field of Classification Search
CPC .................................................... A61P 35/00
See application file for complete search history.

(56) References Cited

U.S. PATENT DOCUMENTS

2021/0171458 A1*  6/2021  Park .......................... A61P 1/00

FOREIGN PATENT DOCUMENTS

KR   10-2014-0141904 A   12/2014
KR   10-2019-0053090 A   5/2019

OTHER PUBLICATIONS

Zhou, Biochemical and Anti-Triple Negative Metastatic Breast Tumor Cell Properties of Psammaplins. 2018. Marine Drugs. 16(11): 442. (Year: 2018).*
Yue, Influence of reduction-sensitive diselenide bonds and disulfide bonds on oligoethylenimine conjugates for gene delivery. 2014. Journal of Materials Chemistry B. 2(41):7210-7221. (Year: 2014).*
Wen, J et al., "Synthesis, Biological Evaluation and Molecular Modeling Studies of Psammaplin A and Its Analogs as Potent Histone Deacetylases Inhibitors and Cytotoxic Agents", Bioorganic & Medicinal Chemistry Letters, 2016, vol. 26 (17), pp. 4372-4376.
Zhou, Y.-D et al., "Biochemical and Anti-triple Negative Metastatic Breast Tumor Cell Properties of Psammaplins", Marine Drugs, 2018, vol. 16(11), No. 442, pp. 1-15.

* cited by examiner

*Primary Examiner* — Jeffrey S Lundgren
*Assistant Examiner* — Eric Tran
(74) *Attorney, Agent, or Firm* — Vorys, Sater, Seymour and Pease LLP; Mih Suhn Koh

(57) ABSTRACT

Provided is a composition for the prevention and treatment of one or more cancers selected from the group consisting of breast cancer, liver cancer, and gastric cancer, the composition comprising selenopsammaplin A as active ingredients. The selenopsammaplin A and derivatives thereof of the present invention have been confirmed to exhibit excellent anticancer activity against breast cancer, liver cancer, and gastric cancer cells, and exhibit not only a strong effect of suppressing breast cancer growth compared to existing psammaplin A but also an excellent effect of suppressing the metastasis of breast cancer cells, and thus the selenopsammaplin A and derivatives thereof are expected to be effectively usable as a pharmaceutical composition for the prevention and treatment of breast cancer, liver cancer, and/or gastric cancer, and for the suppression of breast cancer metastasis.

11 Claims, 23 Drawing Sheets

COMPOSITION FOR PREVENTING AND TREATING BREAST CANCER INCLUDING SELENOPSAMMAPLIN A AS ACTIVE INGREDIENTS

CROSS-REFERENCE TO RELATED APPLICATIONS

This application is a 371 of PCT/KR2019/013461, filed Oct. 15, 2019, which claims the benefit of priority from Korean Patent Application No. 10-2019-0115722 filed Sep. 20, 2019, the contents of each of which are incorporated herein by reference in its entirety.

TECHNICAL FIELD

The present invention relates to a composition for the prevention and treatment of one or more cancers selected from the group consisting of breast cancer, liver cancer, and gastric cancer, the composition comprising selenopsammaplin A as active ingredients, and the like.

This application claims priority to and the benefit of Korean Patent Application No. 10-2019-0115722, filed on Sep. 20, 2019, and the entire contents disclosed in the specification and drawings of the application are incorporated herein by reference.

BACKGROUND ART

Breast cancer is one of the most common cancers, ranking, among female cancers, first in the United States and second in Korea based on 2008 statistics. In Korea, since 2000, the rate of breast cancer incidence has globally increased most rapidly at 6.8% per year (reported by WHO in 2010). In fact, according to statistics from the Korea Health Industry Development Institute in 2012 and 2013, about 885,735 of a total of 3,232,417 patients who received checkups were diagnosed with breast cancer, and are paying the second highest medical expenses among national cancer patients. Considering the rate of increase in breast cancer incidence in Korea, the treatment of breast cancer is very important and the development of a pharmaceutical composition is required.

When breast cancer is treated with an anticancer agent such as taxol or radiation, it seems that the early cancer tissue stops growing and the size of cancer is reduced, but the cancer may grow again after a certain period of time. When cancer cells that have re-grown are treated again with the same anticancer agent, the anticancer agent will no longer act due to becoming resistance, and the metastasis of cancer cells will increase, resulting in a more malignant trait. Triple-negative breast cancer cells are known to be deficient in estrogen and progesterone receptors (ER−/PR−) and not express HER2 (HER2−), and thus have the characteristic of being resistant to taxol, tamoxifen, and the Her2 activity inhibitor (trastuzumab). Moreover, the frequency of incidence of breast cancer occurs mainly in young women under the age of 50 or African-American/Hispanic women with mutated RCA1. In the United States, it is known that triple-negative breast cancer patients account for about 12-17% of all breast cancer patients, and about 15.9% of all breast cancer patients in Korea are reported to have triple-negative breast cancer. The 5-year survival rate of triple-negative breast cancer patients is reported to be about 77%, which is lower than that of patients with other types of breast cancers, i.e., about 93%. In addition, triple-negative breast cancer is more aggressive than other types of breast cancer, such as having a higher histological grade and an invasive ductal carcinoma form, and triple-negative breast cancer has many characteristics similar to basal-like breast cancer subtype, such as no effect by hormone therapy, trastuzumab, or the like, a high degree of aneuploidy, and a similar gene-expression profile.

The limitation of targeted treatment against triple-negative breast cancer is that it is difficult to find a target to be targeted, and thus there is no effective targeted treatment related thereto.

DESCRIPTION OF EMBODIMENTS

Technical Problem

The present invention has been made to meet the above-described need in the prior art, and the inventors of the present invention confirmed that selenopsammaplin A and derivatives thereof not only suppressed the proliferation of breast cancer cells, but also suppressed metastasis and migration, thus confirming the effect of preventing or treating breast cancer and the effect of suppressing breast cancer metastasis, and thus completed the present invention based on these findings.

Therefore, an object of the present invention is to provide a composition for preventing or treating of one or more cancers selected from the group consisting of breast cancer, liver cancer, and gastric cancer, the composition comprising selenopsammaplin A and a derivative thereof, or a pharmaceutically acceptable salt thereof as active ingredients.

Another object of the present invention is to provide a composition for suppressing breast cancer metastasis, comprising selenopsammaplin A and a derivative thereof, or a pharmaceutically acceptable salt thereof as active ingredients.

Another object of the present invention is to provide a use of a pharmaceutical composition comprising selenopsammaplin A and a derivative thereof as active ingredients for preventing or treating one or more cancers selected from the group consisting of breast cancer, liver cancer, and gastric cancer.

Another object of the present invention is to provide a method of preventing or treating one or more cancers selected from the group consisting of breast cancer, liver cancer, and gastric cancer, the method comprising administering, to an individual, a pharmaceutical composition comprising selenopsammaplin A and a derivative thereof as active ingredients.

Another object of the present invention is to provide a use of a pharmaceutical composition comprising selenopsammaplin A and a derivative thereof as active ingredients for suppressing breast cancer metastasis.

Another object of the present invention is to provide a method of suppressing breast cancer metastasis, including administering, to an individual, a pharmaceutical composition comprising selenopsammaplin A and a derivative thereof as active ingredients.

However, technical problems to be solved by the present invention are not limited to the above-described technical problems, and other unmentioned technical problems will become apparent from the following description to those of ordinary skill in the art.

Technical Solution

According to an aspect of the present invention, there is provided a pharmaceutical composition for preventing or treating of one or more cancers selected from the group consisting of breast cancer, liver cancer, and gastric cancer, the composition comprising selenopsammaplin A and a derivative thereof which are represented by Formula 1 below, or a pharmaceutically acceptable salt thereof as active ingredients.

[Formula 1]

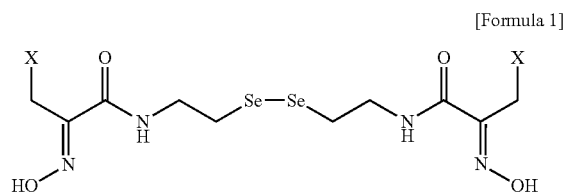

wherein, in Formula 1,
X is hydrogen, a $C_{1-5}$ alkyl,

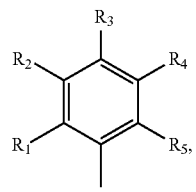

1-naphthyl, 2-naphthyl, or 9-anthracenyl;
  wherein $R_1$ to $R_5$ are each independently hydrogen, nitro, a halogen, cyano, hydroxy, dimethylamino, methylsulfonylamide, trifluoromethyl, a $C_{1-5}$ alkyl, a $C_{1-3}$ alkoxy, vinyl, aryl, phenoxy, or benzoxy;
  when $R_3$ and $R_4$ are linked to form a ring, the resulting structure is

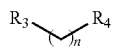

wherein n=1, 2, or 3; and
  when any one of $R_1$ to $R_5$ is phenoxy or benzoxy, a substituent of the aromatic ring is a $C_{1-3}$ alkyl, a $C_{1-3}$ alkoxy, a halogen, trifluoromethyl, or t-butyl.
  In one embodiment of the present invention, X is

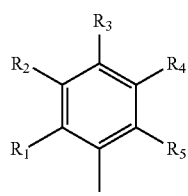

or 2-naphthyl;
  wherein $R_1$, $R_2$, and $R_5$ are each independently hydrogen;
  $R_3$ is hydrogen, hydroxy, ethoxy, t-butyl, fluoro, chloro, bromo, nitro, or benzoxy; and
  $R_4$ may be hydrogen, bromo, chloro, or fluoro, but the present invention is not limited thereto.
  In another embodiment of the present invention, the cancer may be breast cancer, but the present invention is not limited thereto.
  In another embodiment of the present invention, the breast cancer may be triple-negative breast cancer, but the present invention is not limited thereto.

In another embodiment of the present invention, the composition may inhibit DOT1L activity, but the present invention is not limited thereto.

The present invention also provides a pharmaceutical composition for suppressing breast cancer metastasis, comprising selenopsammaplin A and a derivative thereof which are represented by Formula 1, or a pharmaceutically acceptable salt thereof as active ingredients.

In another embodiment of the present invention, the composition may have an effect of suppressing the growth of cancer cells and suppressing invasion and migration, but the present invention is not limited thereto.

The present invention also provides a method of preventing or treating one or more cancers selected from the group consisting of breast cancer, liver cancer, and gastric cancer, the method including administering the pharmaceutical composition comprising selenopsammaplin A and a derivative thereof as active ingredients to an individual in need of treatment for the cancer.

The present invention also provides a use of a pharmaceutical composition comprising selenopsammaplin A and a derivative thereof as active ingredients for preventing or treating one or more cancers selected from the group consisting of breast cancer, liver cancer, and gastric cancer.

The present invention also provides a use of selenopsammaplin A and a derivative thereof for producing a therapeutic agent for one or more cancers selected from the group consisting of breast cancer, liver cancer, and gastric cancer.

The present invention provides a method of treating breast cancer, including administering the pharmaceutical composition comprising selenopsammaplin A and a derivative thereof as active ingredients to an individual in need of treatment for breast cancer metastasis.

The present invention provides a method of suppressing breast cancer metastasis, including administering, to an individual, to the pharmaceutical composition comprising selenopsammaplin A and a derivative thereof as active ingredients.

The present invention also provides a use of the pharmaceutical composition comprising selenopsammaplin A and a derivative thereof as active ingredients for suppressing breast cancer metastasis.

The present invention also provides a use of selenopsammaplin A and a derivative thereof for producing an inhibitor of breast cancer metastasis.

Advantageous Effects of Invention

The present invention has confirmed that, according to research on psammaplin A-related structural activity, a novel compound selenopsammaplin A, the disulfide moiety of which is substituted with diselenide, and derivatives thereof exhibit excellent anticancer activity against breast cancer, liver cancer, and gastric cancer cells, and exhibit not only a superior effect of suppressing the growth of breast cancer to that of existing psammaplin A but also an excellent effect of suppressing the metastasis of breast cancer cells, and thus the selenopsammaplin A and derivatives thereof are expected to be effectively usable as a pharmaceutical composition for preventing and treating breast cancer, liver cancer, and gastric cancer, and suppressing breast cancer metastasis.

BRIEF DESCRIPTION OF DRAWINGS

FIGS. 7A to 7F illustrate results confirming the effect of compound 2 (10 nM) on the expression of EMT markers known to mediate cell metastasis, wherein FIG. 7A illustrates results confirming the mRNA expression level of CDH1 (E-cadherin), FIG. 7B illustrates results confirming the mRNA expression level of CDH2 (N-cadherin), FIG. 7C illustrates results confirming the mRNA expression level of ZEB1, FIG. 7D illustrates results confirming the mRNA expression level of VIM (vimentin), FIG. 7E illustrates results confirming the protein expression levels of CDH1, CDH2, ZEB1, and vimentin, and FIG. 7F illustrates their relative intensities.

FIGS. 8A to 8D illustrate results confirming the possibility of suppressing tumor growth using a xenograft mouse model treated with compound 2 (10 nM), wherein FIG. 8A illustrates tumor volume, FIG. 8B illustrates final tumor weight, FIG. 8C illustrates mouse body weight, and FIG. 8D illustrates the results of photographing tumors.

MODE OF INVENTION

Figure 1:
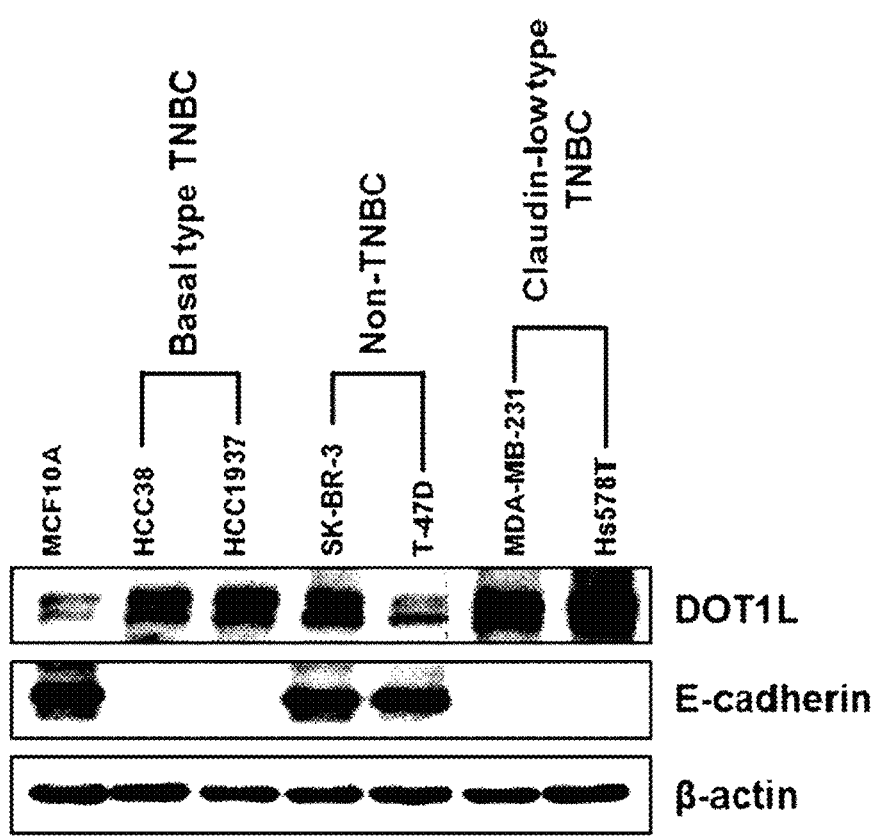
FIG. 1 illustrates results confirming that DOT1L, which is a histone methylation enzyme, is overexpressed in triple-negative breast cancer (TNBC) compared to normal cells (MCF10A) and carcinomas other than triple-negative breast cancer, and E-cadherin, which is a representative marker of cancer metastasis, is conversely lowered.

The inventors of the present invention confirmed that selenopsammaplin A and derivatives thereof effectively suppressed the growth of a breast cancer cell line, effectively suppressed the methylation of a target of DOT1L which is overexpressed in a triple-negative breast cancer cell line, exhibited a very potent effect of suppressing the migration and metastasis of cancer cells compared to psammaplin A, effectively suppressed tumor growth in a breast cancer animal model, and reduced metastasis to the lungs, and thus completed the present invention (see examples of the present invention).

Therefore, the present invention provides a composition for preventing or treating one or more cancers selected from the group consisting of breast cancer, liver cancer, and gastric cancer, the composition comprising selenopsammaplin A, a derivative thereof, or a pharmaceutically acceptable salt thereof as active ingredients.

Hereinafter, the present invention will be described in detail.

The selenopsammaplin A and the derivative thereof of the present invention may be represented by Formula 1:

[Formula 1]

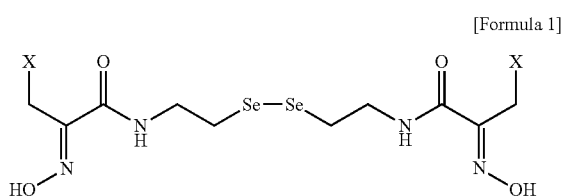

wherein, in Formula 1,

X is hydrogen, a $C_{1-5}$ alkyl,

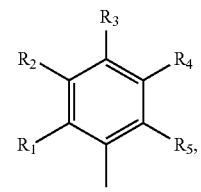

1-naphthyl, 2-naphthyl, or 9-anthracenyl;

wherein $R_1$ to $R_5$ are each independently hydrogen, nitro, a halogen, cyano, hydroxy, dimethylamino, methylsulfonylamide, trifluoromethyl, a $C_{1-5}$ alkyl, a $C_{1-3}$ alkoxy, vinyl, aryl, phenoxy, or benzoxy;

when $R_3$ and $R_4$ are linked to form a ring, the resulting structure is

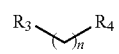

wherein n=1, 2, or 3; and when any one of $R_1$ to $R_5$ is phenoxy or benzoxy, a substituent of the aromatic ring is a $C_{1-3}$ alkyl, a $C_{1-3}$ alkoxy, a halogen, trifluoromethyl, or t-butyl.

Specifically, X is

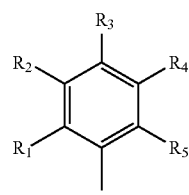

or 2-naphthyl;

wherein $R_1$, $R_2$, and $R_5$ are each independently hydrogen;

$R_3$ is hydrogen, hydroxy, ethoxy, t-butyl, fluoro, chloro, bromo, nitro, or benzoxy; and $R_4$ may be hydrogen, bromo, chloro, or fluoro, but the present invention is not limited thereto.

Hereinafter, the definition of various substituents for preparing the compounds according to the present invention will be provided.

The term "$C_{1-5}$ alkyl" used in the present invention means a monovalent alkyl group having 1 to 5 carbon atoms, and "$C_{1-3}$ alkyl" means a monovalent alkyl group having 1 to 3 carbon atoms. Examples thereof may include functional groups such as methyl, ethyl, n-propyl, i-propyl, n-butyl, i-butyl, tert-butyl, and n-hexyl.

Alkyls described in the present invention, and other substituents containing an alkyl moiety include both linear and branched forms.

The term "$C_{1-3}$ alkoxy" as used in the present invention means an —O—R group, wherein R means "$C_1$-$C_3$ alkyl." Examples of preferable alkoxy groups include methoxy, ethoxy, and phenoxy.

Alkyls and alkoxys described in the present invention, and other substituents containing an alkyl moiety include both linear and branched forms.

The form of X described in the present invention is not limited to the above and may be the same as shown in Table 1 below.

TABLE 1

| Compound | X |
| --- | --- |
| 1 | 2-bromo-4-substituted phenol (OH, Br) |
| 2 | phenyl |
| 3 | 2-naphthyl |
| 4 | 4-fluorophenyl (F) |
| 5 | 3,4-difluorophenyl (F, F) |
| 6 | 4-chlorophenyl (Cl) |
| 7 | 3,4-dichlorophenyl (Cl, Cl) |
| 8 | 4-bromophenyl (Br) |
| 9 | 4-ethoxyphenyl (OEt) |
| 10 | 4-benzyloxyphenyl (OBn) |
| 11 | 4-nitrophenyl ($NO_2$) |
| 12 | 4-tert-butylphenyl |
| 13 | 3-chloro-4-hydroxyphenyl (OH, Cl) |

TABLE 1-continued

| Compound | X |
|---|---|
| 14 | 2-fluoro-4-substituted phenol (OH, F on benzene ring) |

Preferable examples of selenopsammaplin A and derivatives thereof, which are represented by Formula 1, according to the present invention are as follows:

(2E,2'E)-N,N'-(diselenediylbis(ethane-2,1-diyl))bis(3-(3-bromo-4-hydroxyphenyl)-2-(hydroxyimino)propanamide);

(2E,2'E)-N,N'-(diselenediylbis(ethane-2,1-diyl))bis(3-(3-chloro-4-hydroxyphenyl)-2-(hydroxyimino)propanamide);

(2E,2'E)-N,N'-(diselenediylbis(ethane-2,1-diyl))bis(3-(3-fluoro-4-hydroxyphenyl)-2-(hydroxyimino)propanamide);

(2E,2'E)-N,N'-(diselenediylbis(ethane-2,1-diyl))bis(2-(hydroxyimino)-3-phenylpropanamide);

(2E,2'E)-N,N'-(diselenediylbis(ethane-2,1-diyl))bis(3-(4-fluorophenyl)-2-(hydroxyimino)propanamide);

(2E,2'E)-N,N'-(diselenediylbis(ethane-2,1-diyl))bis(3-(4-chlorophenyl)-2-(hydroxyimino)propanamide);

(2E,2'E)-N,N'-(diselenediylbis(ethane-2,1-diyl))bis(3-(4-bromophenyl)-2-(hydroxyimino)propanamide);

(2E,2'E)-N,N'-(diselenediylbis(ethane-2,1-diyl))bis(3-(3,4-difluorophenyl)-2-(hydroxyimino)propanamide);

(2E,2'E)-N,N'-(diselenediylbis(ethane-2,1-diyl))bis(3,4-dichlorophenyl)-2-(hydroxyimino)propanamide);

(2E,2'E)-N,N'-(diselenediylbis(ethane-2,1-diyl))bis(3-(4-ethoxyphenyl)-2-(hydroxyimino)propanamide);

(2E,2'E)-N,N'-(diselenediylbis(ethane-2,1-diyl))bis(3-(4-benzyloxy)phenyl)-2-(hydroxyimino)propanamide);

(2E,2'E)-N,N'-(diselenediylbis(ethane-2,1-diyl))bis(2-(hydroxyimino)-3-(4-nitrophenyl)propanamide);

(2E,2'E)-N,N'-(diselenediylbis(ethane-2,1-diyl))bis(3-(4-tert-butyl)phenyl)-2-(hydroxyimino)propanamide); and (2E,2'E)-N,N'-(diselenediylbis(ethane-2,1-diyl))bis(2-(hydroxyimino)-3-(naphthalene-2-yl)propanamide).

The compound of the present invention may be used in the form of a pharmaceutically acceptable salt, and the salt may be an acid addition salt formed by a pharmaceutically acceptable free acid.

The term "salt" as used in the present invention refers to an acid addition salt formed by a pharmaceutically acceptable free acid. The acid addition salt is obtained from: inorganic acids such as hydrochloric acid, nitric acid, phosphoric acid, sulfuric acid, hydrobromic acid, hydriodic acid, nitrous acid, and phosphorous acid; or nontoxic organic acids such as aliphatic mono- and dicarboxylates, phenyl-substituted alkanoates, hydroxy alkanoates and alkandioates, aromatic acids, and aliphatic and aromatic sulfonic acids. Examples of these pharmaceutically nontoxic salts include sulfates, pyrosulfates, bisulfates, sulfites, bisulfites, nitrates, phosphates, monohydrogen phosphates, dihydrogen phosphates, methaphosphates, pyrophosphate chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butine-1,4-dioates, hexane-1,6-dioates, benzoates, chlorobenzoates, methylbenzoates, dinitro benzoates, hydroxybenzoates, methoxybenzoates, phthalates, terephthalates, benzene sulfonates, toluene sulfonates, chlorobenzene sulfonates, xylenesulfonates, phenyl acetates, phenylpropionates, phenylbutyrates, citrates, lactates, β-hydroxybutyrates, glycolates, maleates, tartrates, methanesulfonates, propanesulfonates, naphthalene-1-sulfonates, naphthalene-2-sulfonates, and mandelates.

The acid addition salt according to the present invention may be prepared by typical methods, for example, dissolving the compound in an excess aqueous acid solution, and precipitating this salt using a water-miscible organic solvent, for example, methanol, ethanol, acetone or acetonitrile. Further, the acid addition salt may also be prepared by evaporating the solvent or excess acid from this mixture, and then drying the mixture or suction-filtering a precipitated salt.

In addition, a pharmaceutically acceptable metal salt may be prepared using a base. An alkali metal or alkaline earth metal salt is obtained by, for example, dissolving the compound in an excess alkali metal hydroxide or alkaline earth metal hydroxide solution, filtering the non-soluble compound salt, evaporating the filtrate, and drying the result product. In this case, preparing a sodium, potassium or calcium salt as the metal salt is pharmaceutically suitable. A silver salt corresponding to this is obtained by reacting the alkali metal or alkaline earth metal salt with a suitable silver salt (for example, silver nitrate).

In addition, the compound of the present invention includes not only pharmaceutically acceptable salts thereof, but also all salts, isomers, hydrates, and solvates that may be prepared using general methods.

The selenopsammaplin A and the derivative thereof of the present invention may be included in an amount of 1 pg w/v % to 30 g w/v % in a composition for the prevention, treatment, or alleviation of breast cancer, liver cancer, and/or gastric cancer and a composition for suppressing breast cancer metastasis, but the present invention is not limited thereto.

The cancer of the present invention may preferably be breast cancer, but the present invention is not limited thereto.

In the present invention, "breast cancer" may be triple-negative breast cancer, but the present invention is not limited thereto.

In the present invention, "cancer metastasis" means that cancer cells spread from a primary tumor to other organs to form new tumors. Metastasis is a major life-threatening phenomenon in a variety of cancer patients, and thus preventing or regulating metastasis is an important goal in the cancer research field. In the case of early diagnosis when metastasis has not occurred, surgery, anticancer treatment, or radiation therapy is effective, whereas in the case of metastasis at diagnosis, the effects of these therapies are reduced. In addition, although metastasis was not confirmed during diagnosis, it is often confirmed during or after treatment. Although the importance of cancer metastasis is clinically high, the metastasis process has not yet been fully understood.

Metastasis consists of successive stages such as invasion, intravasation, arrest, extravasation, and colonization, and through these processes, cancer begins in a primary organ and ultimately forms in other organs. The first stage, invasion, is the initiation of metastasis, including changes in interactions of cancer cells with intercellular or extracellular matrix, degradation of surrounding tissues, migration of cancer cells into tissues, and the like. The second step, intravasation, involves the passage of cancer cells through the blood vessels or endothelial cells of lymphatic vessels into the systematic circulation. It has been confirmed that only a small fraction of introduced cancer cells survive in the circulatory process. Some surviving cancer cells have successful intravasation through the capillary endothelial cells of other sites and adapt to the new environment, proliferating and forming metastatic cancer.

In the present invention, "suppression of breast cancer metastasis" refers to inhibiting the spread of breast cancer to other organs to form new tumors, and the other organs may be, are not limited to, the lungs, liver, pancreas, spleen, and kidneys.

Another embodiment of the present invention relates to a method of preventing or treating one or more cancers selected from the group consisting of breast cancer, liver cancer, and gastric cancer, the method including administering, to an individual in need of treatment for the cancer, the pharmaceutical composition comprising selenopsammaplin A and a derivative thereof as active ingredients.

Another embodiment of the present invention relates to a use of the pharmaceutical composition comprising selenopsammaplin A and a derivative thereof as active ingredients for preventing or treating of one or more cancers selected from the group consisting of breast cancer, liver cancer, and gastric cancer.

Another embodiment of the present invention relates to a use of selenopsammaplin A and a derivative thereof for producing a therapeutic agent for one or more cancers selected from the group consisting of breast cancer, liver cancer, and gastric cancer.

Another embodiment of the present invention relates to a method of treating breast cancer, including administering, to an individual in need of treatment for breast cancer metastasis, the pharmaceutical composition comprising selenopsammaplin A and a derivative thereof as active ingredients.

Another embodiment of the present invention relates to a method of suppressing breast cancer metastasis, including administering, to an individual, the pharmaceutical composition comprising selenopsammaplin A and a derivative thereof as active ingredients.

Another embodiment of the present invention relates to a use of the pharmaceutical composition comprising selenopsammaplin A and a derivative thereof as active ingredients for suppressing breast cancer metastasis.

Another embodiment of the present invention relates to a use of selenopsammaplin A and a derivative thereof for producing a breast cancer metastasis inhibitor.

In the present invention, "individual" is not limited as long as it is a vertebrate, and specifically refers to humans, mice, rats, guinea pigs, rabbits, monkeys, pigs, horses, cows, sheep, antelopes, dogs, cats, fish, and reptiles, and preferably, may be humans.

In the present invention, "administration" means introducing the pharmaceutical composition of the present invention into a patient by use of an appropriate method, and the composition of the present invention may be orally or parenterally administered via various routes as long as they allow the composition to reach target tissues.

In the present invention, "prevention" means all actions that delay breast cancer or breast cancer metastasis via administration of the composition according to the present invention, "treatment" means all actions that alleviate or beneficially change symptoms due to breast cancer via administration of the pharmaceutical composition according to the present invention, and "alleviation" means all actions that reduce the parameters related to breast cancer, for example, the severity of a symptom via administration of the composition according to the present invention.

In the present invention, the pharmaceutical composition may further include a suitable carrier, excipient, and diluent commonly used in the preparation of pharmaceutical compositions.

In the present invention, "carrier," which is also referred to as a vehicle, means a compound that facilitates the delivery of a protein or a peptide into a cell or tissue, and for example, dimethyl sulfoxide (DMSO) is a commonly used carrier that facilitates the delivery of many organic materials into a cell or tissue of a living organism.

In the present invention, "diluent" is defined as a compound that is diluted in water that not only stabilizes the biologically active form of a target compound, but also dissolves the compound. Salts dissolved in buffer solutions are used as diluents in the art. A commonly used buffer solution is phosphate-buffered saline because it mimics the salt state of human body fluids. Since buffer salts are able to control the pH of a solution at low concentrations, buffer diluents rarely modify the biological activity of the compound. Compounds including azelaic acid as used herein may be administered to a human patient as it is, or as a pharmaceutical composition mixed with other ingredients or with a suitable carrier or excipient as in combined therapy.

In addition, the pharmaceutical composition comprising selenopsammaplin A and a derivative thereof as active ingredients, according to the present invention, may be used after being formulated, using general methods, in the form of preparations for external application such as powders, granules, tablets, capsules, suspensions, emulsions, syrups, and aerosols, and sterile injection solutions, and examples of the carrier, the excipients, and the diluent that may be included in the composition may include lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. For the formulation thereof, diluents or excipients such as fillers, extenders, binders, wetting agents, disintegrating agents, and surfactants are used. Solid preparations for oral administration include tablets, pills, powders, granules, capsules, and the like, and such solid preparations are formulated by mixing the composition with at least one excipient, e.g., starch, calcium carbonate, sucrose, lactose, and gelatin. In addition to simple excipients, lubricants such as magnesium stearate and talc are also used. Examples of liquid preparations for oral administration include suspensions, liquids for internal use, emulsions, syrups, and the like, and these liquid preparations may include, in addition to simple commonly used diluents, such as water and liquid paraffin, various types of excipients, for example, a wetting agent, a sweetener, a flavoring agent, and a preservative. Preparations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate. Examples of suppository bases include Witepsol, Macrogol, Tween 61, cacao butter, laurin, glycerogelatin, and the like.

The pharmaceutical composition of the present invention may be administered orally or parenterally, preferably parenterally, and for parenteral administration, may be administered via intramuscular injection, intravenous injection, subcutaneous injection, intraperitoneal injection, topical administration, transdermal administration, or the like.

A suitable dose of the pharmaceutical composition of the present invention may vary depending on factors such as formulation method, administration method, the age, body weight, and gender of a patient, pathological conditions, diet, administration time, administration route, excretion speed, and reaction sensitivity.

The pharmaceutical composition of the present invention may be formulated using a pharmaceutically acceptable carrier and/or an additive according to a method that may be easily carried out by one of ordinary skill in the art to which the present invention pertains to be prepared in a unit dose form or to be contained in a multi-dose container. In this regard, the formulation may be in the form of a solution in oil or an aqueous medium, a suspension, an emulsifying solution, or may also be in the form of an extract, powder, granules, tablets, or capsules, and may further include a dispersing agent or a stabilizing agent.

Suitable individuals to be treated according to the present invention include mammalian individuals. The mammals according to the present invention include, but are not limited to, humans, canine, feline, bovine, caprine, equine, ovine, porcine, rodents, lagomorphs, primates, and the like, and also include in utero mammals. The individual may be any sex and at any stage of development.

All documents mentioned herein are incorporated herein by reference. When introducing elements of the present invention or the exemplary embodiments thereof, the articles "a", "an", "the," and "said" are intended to mean that there are one or more elements. The terms "comprising," "including," and "having" are intended to be inclusive and mean that there may be additional elements other than the listed elements. Although the present invention is described with respect to particular aspects, it should not be construed as limiting the details of these aspects.

Hereinafter, exemplary examples will be described to aid in understanding of the present invention. However, the following examples are provided merely to facilitate the understanding of the present invention and are not intended to limit the scope of the present invention.

Example 1. Confirmation of Expression of DOT1L Protein

Example 1-1. Confirmation of DOT1L Protein Expression in Breast Cancer Cell Line To confirm the DOT1L expression level of a human breast cancer cell line and a normal breast cell line, an experiment was performed as follows. A breast cancer cell line and a normal breast cell line were spread at a concentration of $1 \times 10^6$ cells in a 100 mm culture dish with RPMI and DMEM medium containing 10% FBS, and cultured for 24 hours at 37° C. under a 5% $CO_2$ condition, followed by washing twice with phosphate-buffered saline (PBS). Attached cells were recovered and washed twice with PBS, and then boiling 2× sample loading buffer (250 mM Tris-HCl (pH 6.8), 4% SDS, 10% glycerol, 0.006% bromophenol blue, 2% β-mercaptoethanol, 50 mM sodium fluoride, and 5 mM sodium orthovanadate) was added thereto to disrupt the cells and the cells were left at 100° C. for 10 minutes. After cooling, the cells were stored at 20° C. and lysed at 37° C. immediately before use in protein quantification and electrophoresis. 10 μg of proteins were electrophoresed at 100 V for 2 hours using an 8% SDS-polyacrylamide gel (#456-1036, Bio-Rad, Hercules, Calif.). The separated proteins were transferred to a PVDF membrane (ISEQ15150, Millipore, Bedford, Mass.) at 100 V for 1 hour, and a blocking buffer (5% non-fat dry milk in TBS containing 0.1% Tween-20 (TBST)) was injected thereinto to culture the proteins at room temperature for 1 hour. After washing three times with TBST for 5 minutes, the corresponding single antibody was diluted with 5% non-fat dry milk in TBST and allowed to react with the membrane at 4° C. for 18 hours.

The membrane [ISEQ 1S150, Millipore, Bedford, Mass.] was washed three times with TBST for 10 minutes, and then horseradish peroxidase (HRP)-conjugated secondary antibodies were diluted with 2.5% non-fat dry milk in TBST at a ratio of 1:1,000 and allowed to react with the membrane at room temperature for 2 hours. After washing three times with TBST for 10 minutes, the reaction product was treated with a chemiluminescent reagent (LabFrontier, Suwon, Korea) to confirm the protein expression levels of DOT1L, E-cadherin, and β-actin using LAS-4000 (Fuji Film Corp., Japan), which are illustrated in FIG. 1.

As illustrated in FIG. 1, it was confirmed that the histone methylation enzyme DOT1L was overexpressed in triple-negative breast cancer (TNBC) compared to normal cells (MCF10A) and carcinomas other than triple-negative breast cancer, and accordingly, E-cadherin, which is a representative cancer metastasis marker, was conversely reduced.

Figure 2:
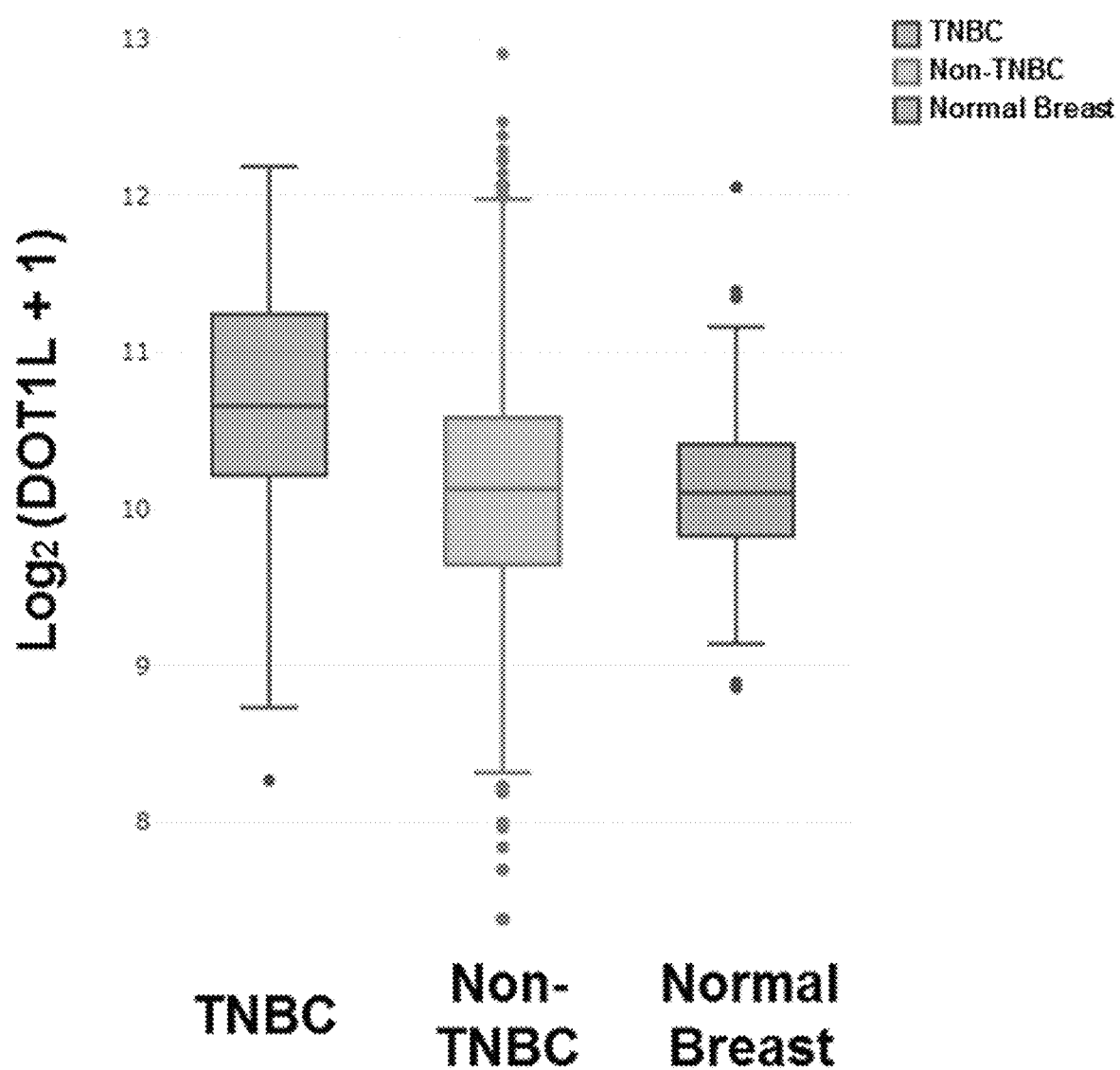
FIG. 2 illustrates results confirming through TGCA database analysis that DOT1L is overexpressed in TNBC even in actual clinical sample analysis.

Example 1-2. Confirmation of DOT1L Protein Expression in Samples of Triple-Negative Breast Cancer Patients As illustrated in FIG. 2, in actual clinical sample analysis using the Cancer Genome Atlas (TCGA), which is a database of the National Cancer Institute, it was also confirmed that DOT1L was overexpressed in TNBC, and thus it is expected that DOT1L can be used as a biomarker of triple-negative breast cancer.

Example 2. Confirmation of Effect of Suppressing Cancer Cell Growth

A cytotoxicity test was performed using synthesized selenopsammaplin A and derivatives thereof (Lee S K et al (2008) Chem Biol Interact 115:215-28).

The cytotoxicity test was performed on a total of five representative cancer cell lines. The cytotoxicity of each compound was measured using an SRB assay method (human lung cancer cells, A549; human colon cancer cells, HCT116; human breast cancer cells, MDA-MB231; human liver cancer cells, SK-HEP-1; human gastric cancer cells, SNU638).

Each cell line was sub-cultured once or twice using Roswell Park Memorial Institute (RPMI) medium 1640 (RPMI 1640) or Dulbecco's Modified Eagle's Medium (DMEM) containing 10% fetal bovine serum (FBS) inactivated by heat, 100 units/mL of penicillin, 100 μg/mL of streptomycin, and 250 ng/mL of amphotericin B at 37° C. for 1 week under a 5% $CO_2$ condition. All cells were lysed in liquid nitrogen, and then passaged three or more times to be used in the experiment. The effects of compounds on cell growth were measured using a sulforhodamine B (SRB) method (Lee et al (1998) Chemico-Biol Interact 115:215-228).

Specifically, each human cancer cell line used in the present invention was sub-cultured in an RPMI medium containing 10% FBS, 1% PSF, and the like, and 10 μl of a sample dissolved in 10% DMSO and 190 μl ($4-5 \times 10^4$ cells/ml) of the cell suspension were added to each well of a 96-well plate and cultured for 3 days. 190 μl of the cell suspension was added to at least 16 wells and cultured for 30 minutes, and used as a zero-day control. The cultured cells were fixed with 10% trichloroacetic acid (TCA) and then stained with an SRB solution, and the staining solution was dissolved with 10 mM Tris-base, and then absorbance at 515 nm was measured. Using the case of culturing in 10% DMSO as a control, cell viability according to each test material treatment was measured using Equation 1 below. Etoposide was used as a positive control.

% Viability=(OD(sample)−OD(0-day))/(OD(10% DMSO)−OD(0-day))×100    [Equation 1]

Assuming that a control not-treated with the sample was set at 100%, the values of sample-treated groups were expressed as percentage with respect to the control, and each test material treatment results were obtained as the mean±SEM of two or three tests. The $IC_{50}$ value is the concentration of the test material for a 50% survival rate. The effects of compounds on the cancer cell lines are shown in Table 2 below.

As shown in Table 2, it was confirmed that the compounds of the present invention effectively suppressed the growth of cancer cells.

is an intracellular DOT1L target, an experiment was performed as follows. The triple-negative breast cancer cell line MDA-MB-231 was spread at a concentration of $2\times10^6$ cells/well on a DMEM medium containing 10% FBS in a 6-well plate, cultured at 37° C. for 24 hours under a 5% $CO_2$ condition, and then washed twice with phosphate-buffered saline (PBS). Attached cells were recovered and washed twice with PBS, and then boiling 2× sample loading buffer (250 mM Tris-HCl (pH 6.8), 4% SDS, 10% glycerol, 0.006% bromophenol blue, 2% β-mercaptoethanol, 50 mM sodium fluoride, and 5 mM sodium orthovanadate) was added thereto to disrupt the cells and the cells were left at 100° C. for 10 minutes. After cooling, the cells were stored at 20° C. and lysed at 37° C. immediately before use in protein quantification and electrophoresis. 10 μg of proteins were electrophoresed at 100 V for 2 hours using a 12% SDS-polyacrylamide gel (#456-1036, Bio-Rad, Hercules, Calif.). The separated proteins were transferred to a PVDF membrane (ISEQ15150, Millipore, Bedford, Mass.) at 100 V for 1 hour, and a blocking buffer (5% non-fat dry milk in TBS containing 0.1% Tween-20 (TBST)) was injected thereinto to culture the proteins at room temperature for 1 hour. After washing three times with TBST for 5 minutes, the corresponding single antibody was diluted with 5% non-fat

TABLE 2

| | X | A549[b] | HCT116[c] | MDA-MB231[d] | SK-HEP-1[e] | SNU638[f] |
|---|---|---|---|---|---|---|
| 1 | 3-Br-4-OH—Ph (9) | 0.03 | 0.01 | 0.16 | 0.21 | 0.02 |
| 2 | Ph (10) | 0.08 | 0.09 | 0.06 | 0.12 | 0.05 |
| 3 | β-napthyl (11) | 0.38 | 0.12 | 0.19 | 0.17 | 0.27 |
| 4 | 4-F—Ph (12) | 0.10 | 0.11 | 0.13 | 0.14 | 0.07 |
| 5 | 3,4-$F_2$—Ph (13) | 0.33 | 0.18 | 0.42 | 0.27 | 0.05 |
| 6 | 4-Cl—Ph (14) | 0.25 | 0.28 | 0.33 | 0.33 | 0.22 |
| 7 | 3,4-$Cl_2$—Ph (15) | 0.28 | 0.52 | 0.25 | 0.32 | 0.18 |
| 8 | 4-Br—Ph (16) | 0.31 | 0.17 | 0.39 | 0.31 | 0.15 |
| 9 | 4-EtO—Ph (17) | 0.05 | 0.07 | 0.20 | 0.18 | 0.03 |
| 10 | 4-BnO—Ph (18) | 0.14 | 0.10 | 0.14 | 0.28 | 0.41 |
| 11 | 4-Nitro—Ph (19) | 0.09 | 0.09 | 0.09 | 0.17 | 0.06 |
| 12 | 4-t-Bu—Ph (20) | 0.10 | 0.13 | 0.10 | 0.19 | 0.28 |
| 13 | 3-Cl-4-OH—Ph (21) | 0.02 | 0.01 | 0.17 | 0.11 | 0.01 |
| 14 | 3-F-4-OH—Ph (22) | 0.02 | 0.01 | 0.19 | 0.13 | 0.02 |
| 15 | Psammaplin A (PsA) | 1.76 | 0.61 | 1.31 | 1.29 | 0.56 |
| 16 | Etoposide | 0.30 | 1.20 | 8.70 | 0.40 | 0.20 |

Example 3. Confirmation of Inhibition of DOT1L Methylation

As confirmed in Example 1, based on the finding that DOT1L was overexpressed in the breast cancer cell line, the effects of the derivatives of the present invention on the methylation of the histone 3 lysine 79 (H3K79) residue, which is an in-vivo target of DOT1L, were examined by western blotting.

Figure 3:
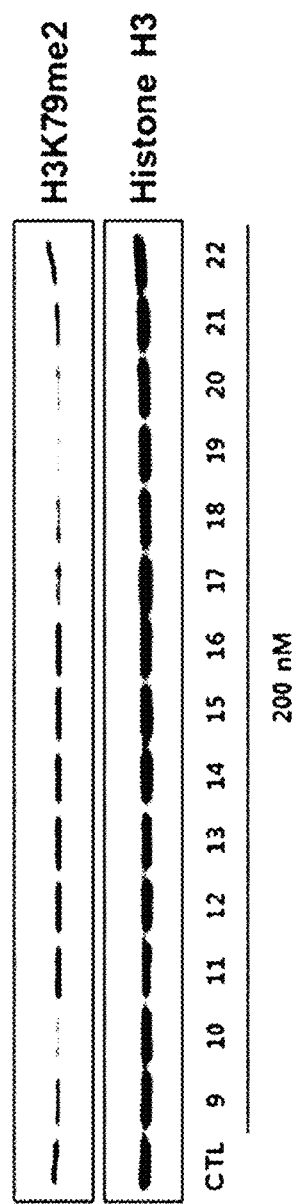
FIG. 3 illustrates results confirming that selenopsammaplin A derivatives of the present invention effectively suppress the methylation of the histone 3 lysine 79 (H3K79) residue, which is an in-vivo target of DOT1L.

As illustrated in FIG. 3, it was confirmed that the compounds of the present invention effectively suppressed H3K79 methylation, and particularly, the inhibitory effects of compound 1(9), compound 2(10), compound 9(17), compound 10(18), compound 11(19), and compound 12(20) were excellent.

Example 4. Confirmation of In-vivo Target Selectivity in MDA-MB-231 Cell Line

Figure 4A:
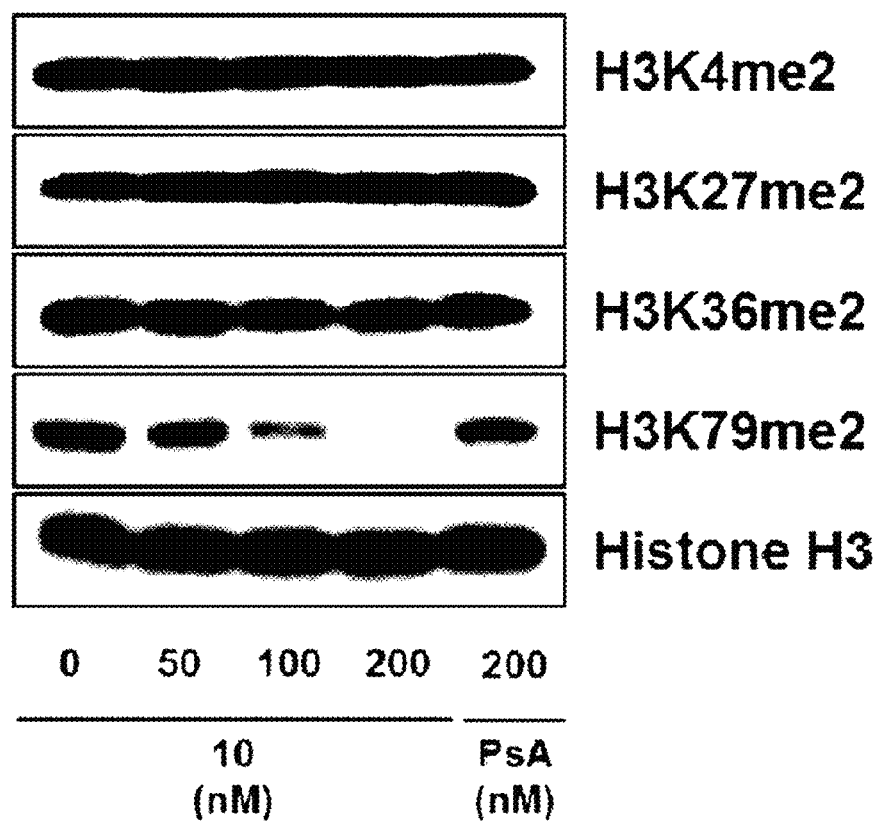
FIGS. 4A and 4B illustrate results confirming that, compared to psammaplin A as a control, compound 2 (10 nM) not only suppresses H3K79 methylation, but also exhibits excellent target selectivity.
Figure 4B:
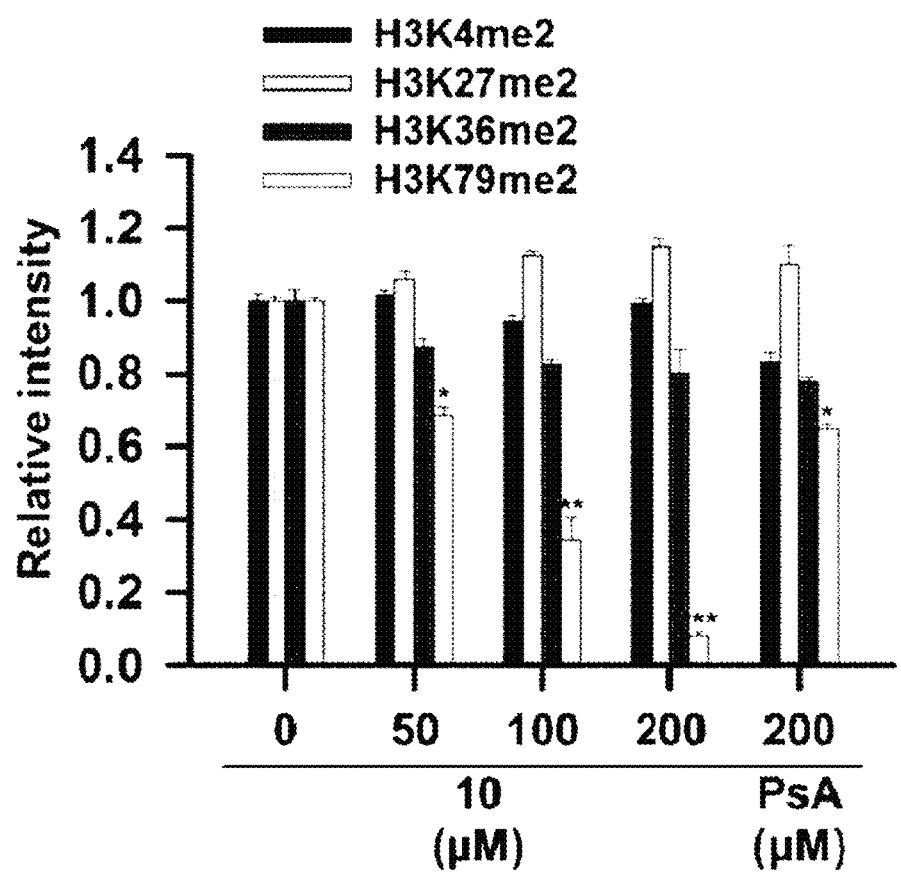

Compound 2 (X=ph) was selected from among selenopsammaplin A and the derivatives thereof, and in order to confirm the selectivity thereof for the H3K79 residue, which dry milk in TBST and allowed to react with the membrane at 4° C. for 18 hours. The membrane [ISEQ 1S150, Millipore, Bedford, Mass.] was washed three times with TBST for 10 minutes, and then horseradish peroxidase (HRP)-conjugated secondary antibodies were diluted with 2.5% non-fat dry milk in TBST at a ratio of 1:2,000 and allowed to react with the membrane at room temperature for 2 hours. After washing three times with TBST for 10 minutes, the reaction product was treated with a chemiluminescent reagent (LabFrontier, Suwon, Korea) to confirm the protein expression levels of H3K4me2, H3K27me2, H3K36me2, H3K79me2, and Histone H3 using LAS-4000 (Fuji Film Corp., Japan), which are illustrated in FIG. 4A. These were quantified using ImageJ software and the results thereof are illustrated in FIG. 4B.

As illustrated in FIG. 4, it was confirmed that, without changing the degrees of methylation of other histone 3 residues, compound 2 specifically suppressed the methylation of residue 79, and such an effect was remarkably strong compared to psammaplin A (PsA).

Example 5. Effect of Suppressing Cancer Cell Migration

To confirm the effects of selenopsammaplin A and derivatives thereof on suppressing breast cancer metastasis, the cancer cell migration suppression effects of the compounds of the present invention were examined.

Figure 5A:
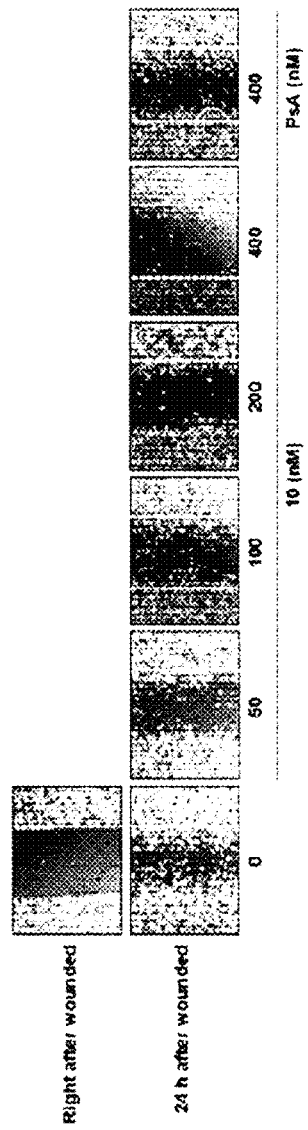
FIGS. 5A and 5B illustrate results confirming the extent to which compound 2 (10 nM) suppresses the migration of cancer cells, which is an index of cancer metastasis.
Figure 5B:
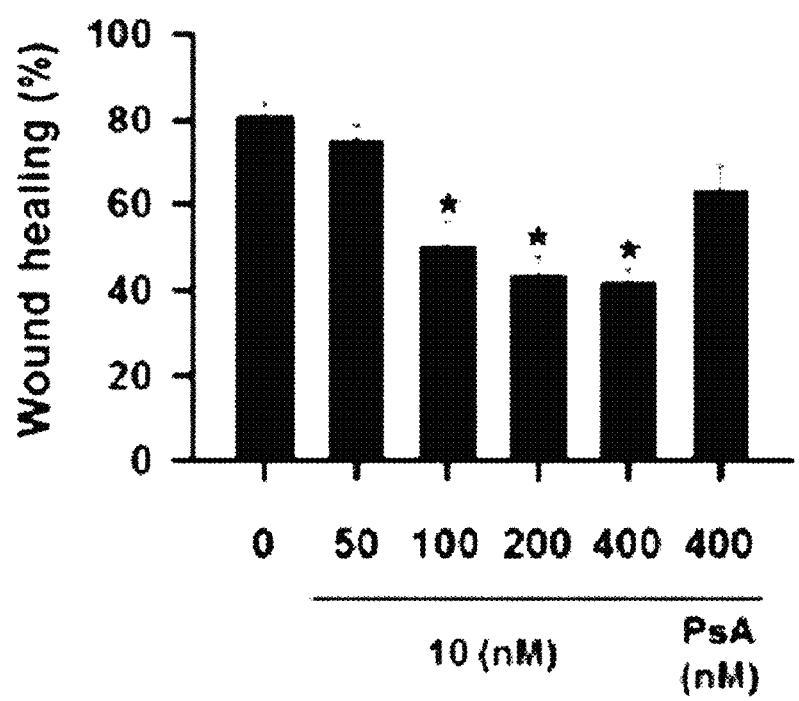

The triple-negative breast cancer cell line MDA-MB-231 was spread at a concentration of $2\times10^6$ cells/well on a DMEM medium containing 10% FBS in a 6-well plate, cultured at 37° C. for 24 hours under a 5% $CO_2$ condition, and then washed once with phosphate-buffered saline (PBS). After scratching using a 200 µl tip, the cells were treated with 50-400 nM compound 2 and 400 nM psammaplin A, and then cultured for 24 hours. After washing once with PBS, the degree of migration of cells was photographed using a microscope, and the results thereof are illustrated in FIG. 5A. The degree of scratch healing compared to a control using ImageJ software is illustrated in FIG. 5B.

As illustrated in FIG. 5, it was confirmed that compound 2 effectively suppressed the migration of breast cancer cells in a concentration-dependent manner.

Example 6. Effect of Suppressing Cancer Cell Invasion

To confirm the effects of selenopsammaplin A and derivatives thereof on suppressing breast cancer metastasis, the cancer cell invasion suppression effects of the compounds of the present invention were examined.

Figure 6A:
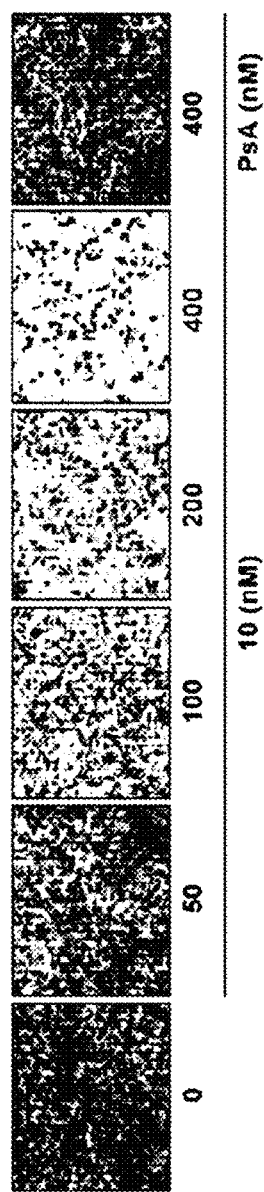
FIGS. 6A and 6B illustrate results confirming the extent to which compound 2 (10 nM) suppresses the invasion of cancer cells, which is an index of cancer metastasis.
Figure 6B:
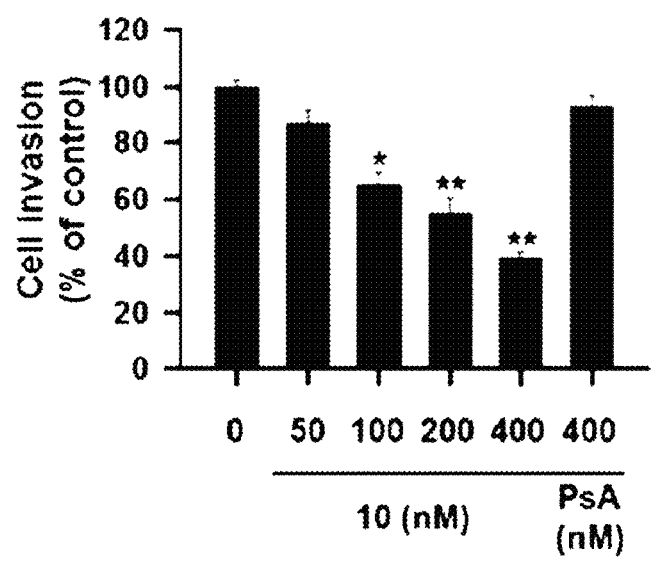

The triple-negative breast cancer cell line MDA-MB-231 was spread at a concentration of $1\times10^6$ cells/well on a DMEM medium containing 10% FBS in a Transwell plate, cultured at 37° C. for 24 hours under a 5% $CO_2$ condition, and then washed once with phosphate-buffered saline (PBS). Subsequently, the cells were treated with 50-400 nM compound 2 and 400 nM psammaplin A, and then cultured for 24 hours. After washing once with PBS, a membrane was attached to a slide glass, the degree of cell invasion was photographed using a microscope, and the results thereof are illustrated in FIG. 6A. The degree of invasion compared to a control using ImageJ software is illustrated in FIG. 6B.

As illustrated in FIG. 6, it was confirmed that compound 2 effectively suppressed the invasion of breast cancer cells in a concentration-dependent manner.

Example 7. Confirmation of Expression of Cancer Cell Metastasis-Mediating EMT Markers The effects of the compounds of the present invention on changes in expression of EMT markers, which are known to mediate cell metastasis, were examined.

Example 7-1. Confirmation of Gene Expression of Cancer Cell Metastasis-Mediating EMT Markers To confirm the EMT-related gene expression levels of the human breast cancer cell line MDA-MB-231, an experiment was performed as follows. To examine the EMT marker expression levels of the human breast cancer cell line MDA-MB-231, breast cancer cells were spread at a concentration of $1\times10^6$ cells/well on an RPMI medium containing 10% FBS in a 100 mm culture dish, cultured at 37° C. for 24 hours under a 5% $CO_2$ condition, and then washed twice with phosphate-buffered saline (PBS). Attached cells were washed twice with PBS, the TRI reagent (TRIzol (#15596-026, Invitrogen, Grand Island, N.Y.)) was used to disrupt the cells, and then $CHCl_3$ was added thereto to extract RNA, followed by precipitation using isopropyl alcohol. The RNA precipitate was washed with 70% ethanol, dried in air, and then lysed using nuclease-free water (AM9937, Ambion, Austin, Tex.), followed by heating at 55° C. for 10 minutes and heat treatment at 70° C. for 5 minutes, so that RNA was present in a single strand state. Total RNA was quantified using NanoDrop (ND-1000, Dae Myung Science, Seoul, Korea) and diluted to 1 µg/µL, and then cDNA was produced using Avian Myeloblastosis Virus (AMV) Reverse Transcriptase (M5108, Promega, Madison, Wis.) and an oligo (dT)15 primer (C110B, Promega, Madison, Wis.). A target gene was amplified in a MiniOpticon™ Real-time PCR Detection system (CFB-3120, Bio-Rad, Hercules, Calif.) using iQTM SYBR Green Supermix (#170-8880, Bio-Rad, Hercules, Calif.) and target gene-specific primers. Real-time PCR conditions were as follows: a PCR cycle of denaturation at 95° C. for 20 seconds; denaturation at 95° C. for 20 seconds; annealing at 56° C. for 20 seconds; and elongation at 72° C. for 30 seconds, and the PCR cycle was repeated 40 times, followed by the final process at 95° C. for 1 minute and at 55° C. for 1 minute. Ct values were determined by the method according to Livak K J et al ((1996) Method 25:402-408) using MJ Opticon Monitor software (Opticon Monitor 3.1.32, Bio-Rad, Hercules, Calif.), and calibrated with the Ct value of β-actin of the sample, and the mRNA expression of EMT markers in the breast cancer cell line is illustrated in FIGS. 7A to 7D.

As illustrated in FIGS. 7A to 7D, it was confirmed that compound 2 increased the expression of E-cadherin, which reduces metastasis, and suppressed the mRNA expression of N-cadherin, ZEB1, and vimentin, which increase metastasis.

Figure 7A:
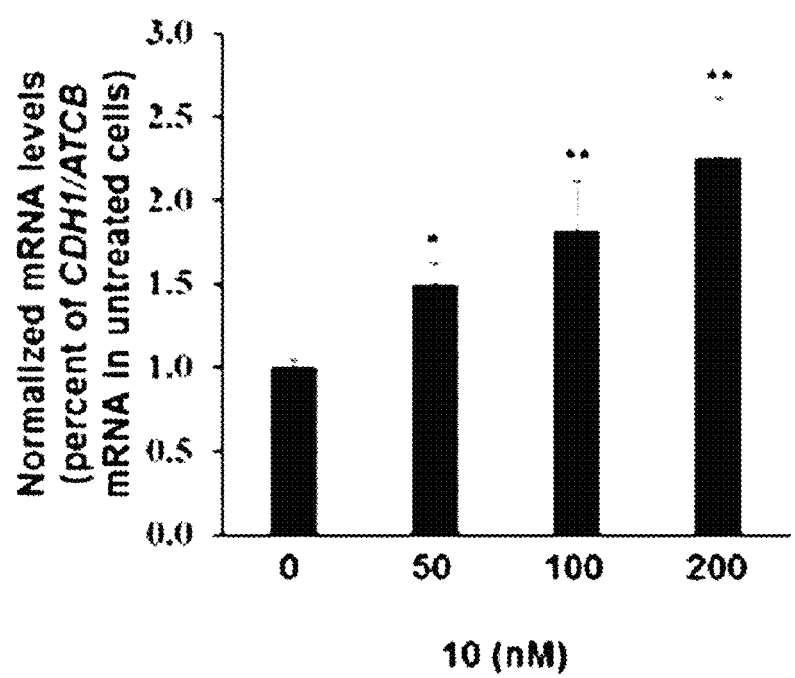
Figure 7B:
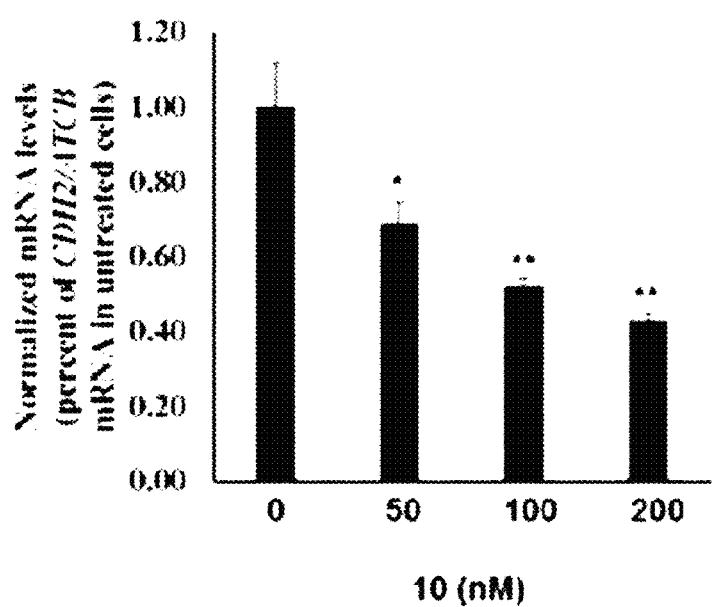
Figure 7C:
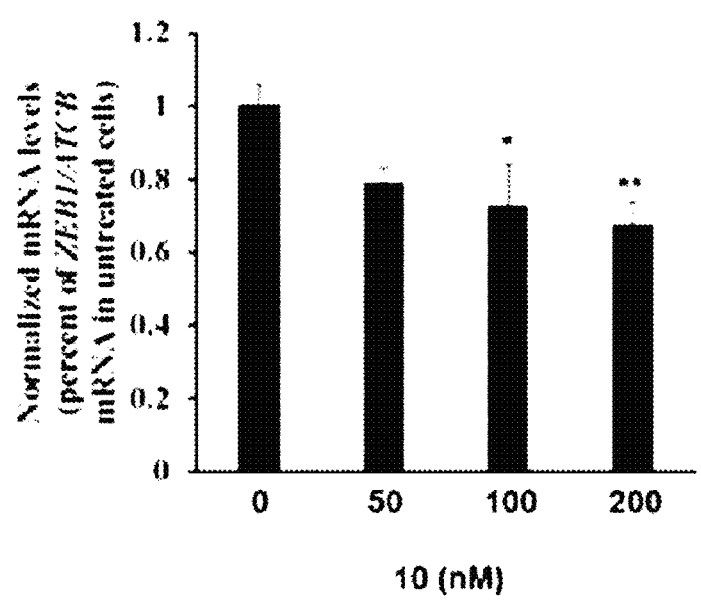
Figure 7D:
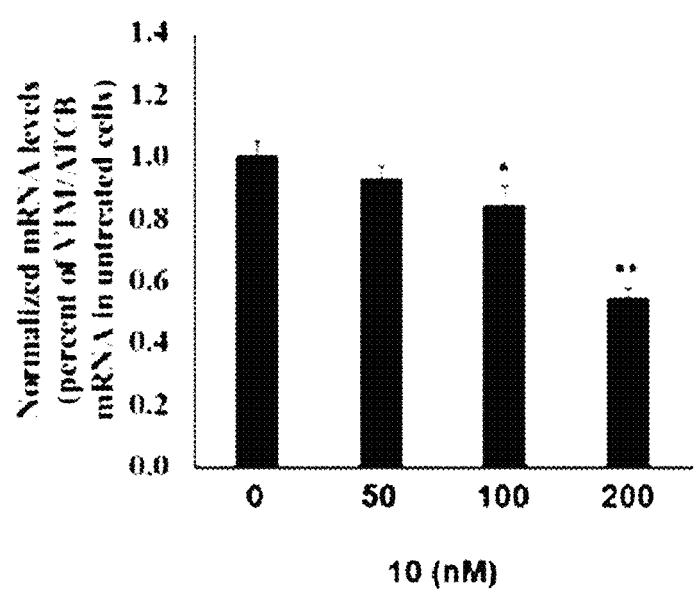
Figure 7E:
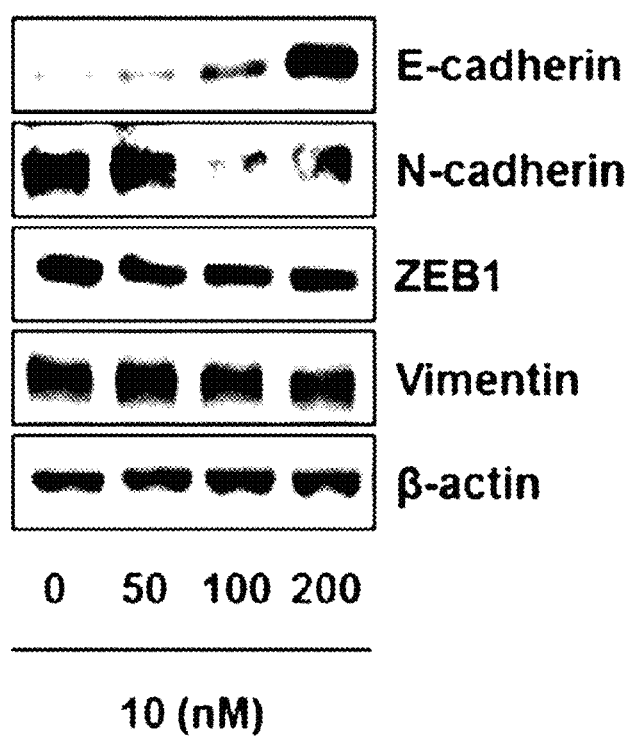

Example 7-2. Confirmation of Protein Expression of Cancer Cell Metastasis-Mediating EMT Markers The triple-negative breast cancer cell line MDA-MB-231 was spread at a concentration of $2\times10^6$ cells/well on a DMEM medium containing 10% FBS in a 6-well plate, cultured at 37° C. for 24 hours under a 5% $CO_2$ condition, and then washed twice with phosphate-buffered saline (PBS). Attached cells were recovered and washed twice with PBS, and then boiling 2× sample loading buffer (250 mM Tris-HCl (pH 6.8), 4% SDS, 10% glycerol, 0.006% bromophenol blue, 2% β-mercaptoethanol, 50 mM sodium fluoride, and 5 mM sodium orthovanadate) was added thereto to disrupt the cells and the cells were left at 100° C. for 10 minutes. After cooling, the cells were stored at 20° C. and lysed at 37° C. immediately before use in protein quantification and electrophoresis. 10 µg of proteins were electrophoresed at 100 V for 2 hours using a 12% SDS-polyacrylamide gel (#456-1036, Bio-Rad, Hercules, Calif.). The separated proteins were transferred to a PVDF membrane (ISEQ15150, Millipore, Bedford, Mass.) at 100 V for 1 hour, and a blocking buffer (5% non-fat dry milk in TBS containing 0.1% Tween-20 (TBST)) was injected thereinto to culture the proteins at room temperature for 1 hour. After washing three times with TBST for 5 minutes, the corresponding single antibody was diluted with 5% non-fat dry milk in TBST and allowed to react with the membrane at 4° C. for 18 hours. The membrane [ISEQ 1S150, Millipore, Bedford, Mass.] was washed three times with TBST for 10 minutes, and then horseradish peroxidase (HRP)-conjugated secondary antibodies were diluted with 2.5% non-fat dry milk in TBST at a ratio of 1:2,000 and allowed to react with the membrane at room temperature for 2 hours. After washing three times with TBST for 10 minutes, the reaction product was treated with a chemiluminescent reagent (Lab-Frontier, Suwon, Korea) to confirm the protein expression levels of E-cadherin, N-cadherin, vimentin, and beta-actin (Fuji Film Corp., Japan) using LAS-4000 (Fuji Film Corp., Japan), and the results thereof are illustrated in FIG. 7E. The proteins were quantified using ImageJ software, which are illustrated in FIG. 7F.

Figure 7F:
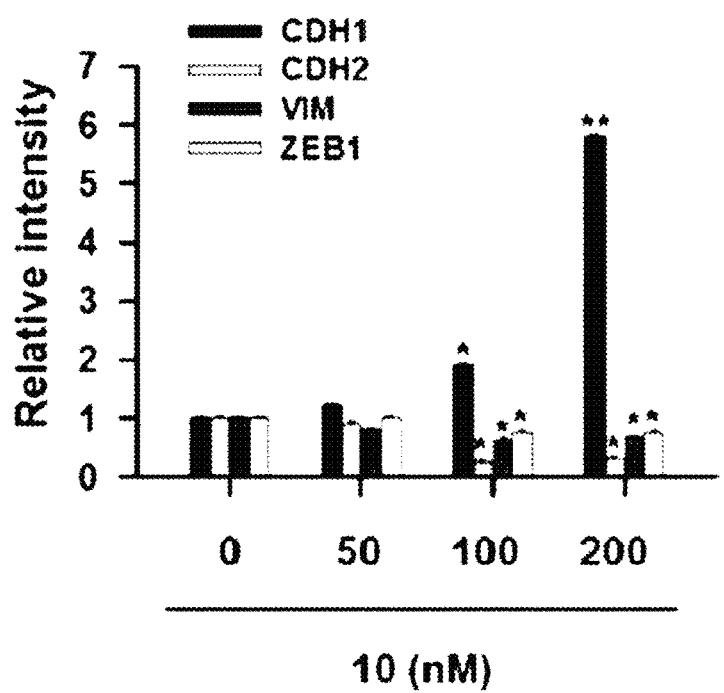

As illustrated in FIGS. 7E and 7F, it was also confirmed that compound 2 increased the expression of E-cadherin, which reduces metastasis, and suppressed the mRNA expression of N-cadherin, ZEB1, and vimentin.

Example 8. Effect of Suppressing Growth of Breast Tumor

The effect of suppressing the growth of breast tumors was examined using an animal model.

Figure 8A:
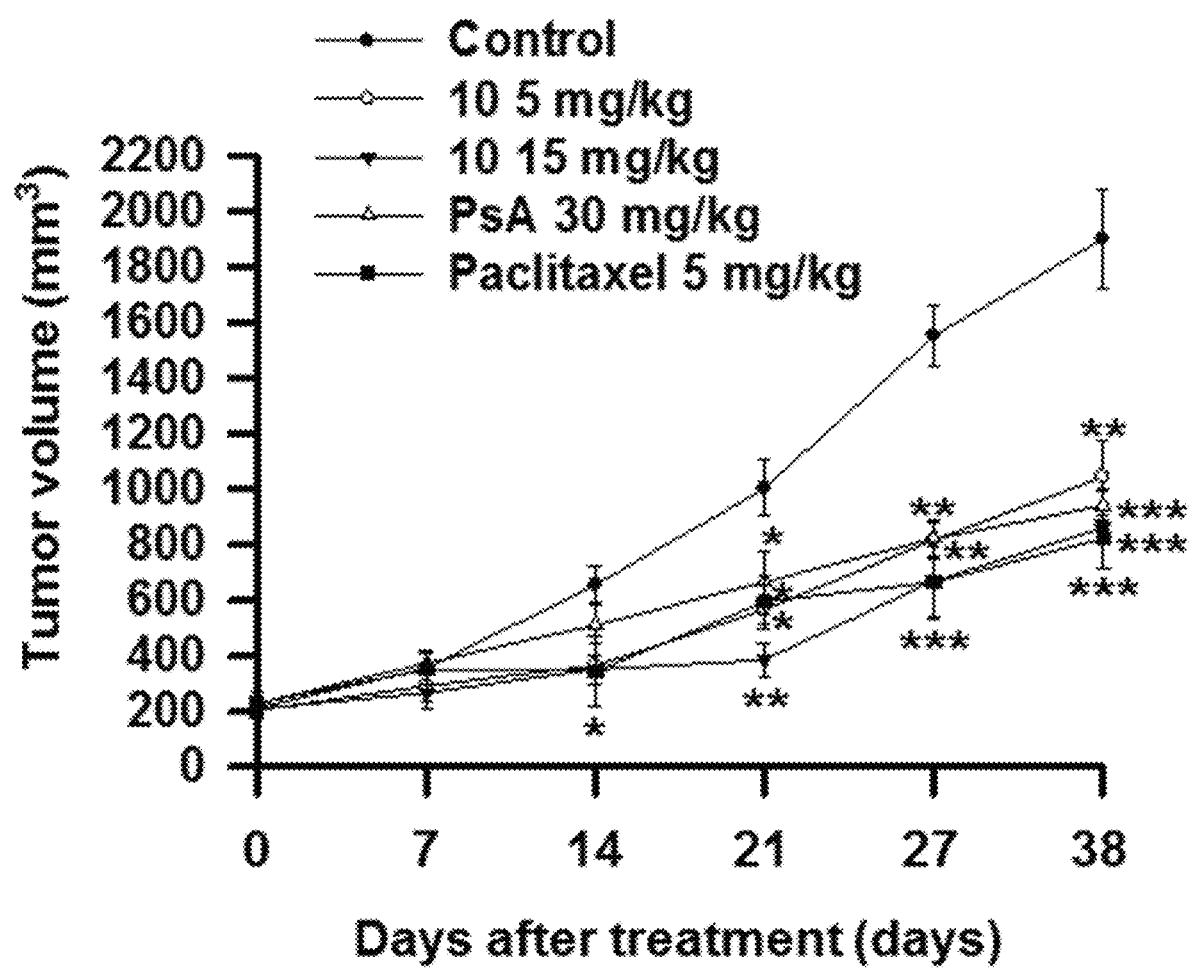
Figure 8B:
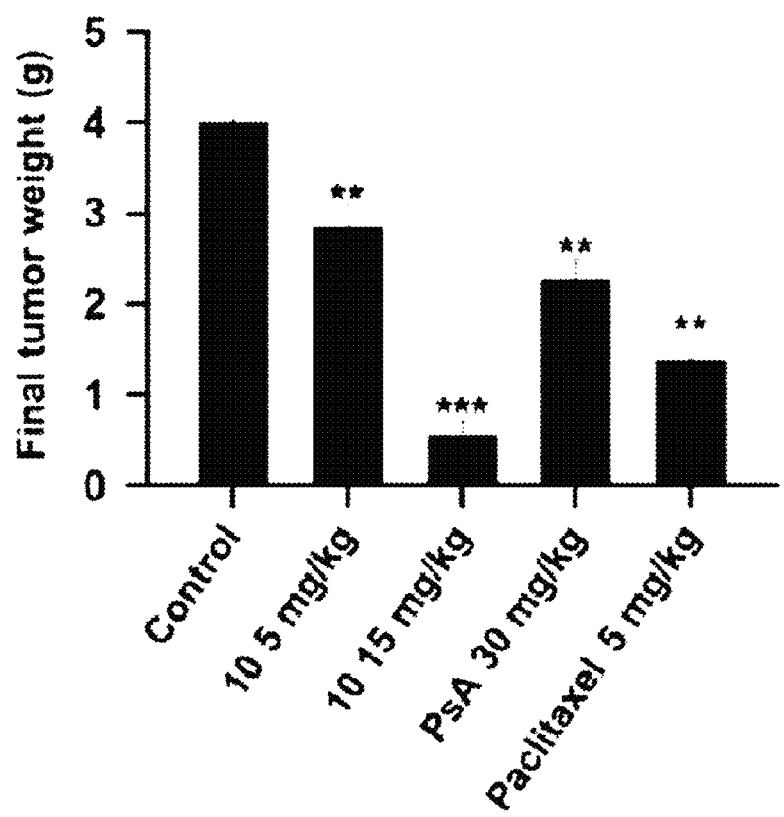
Figure 8C:
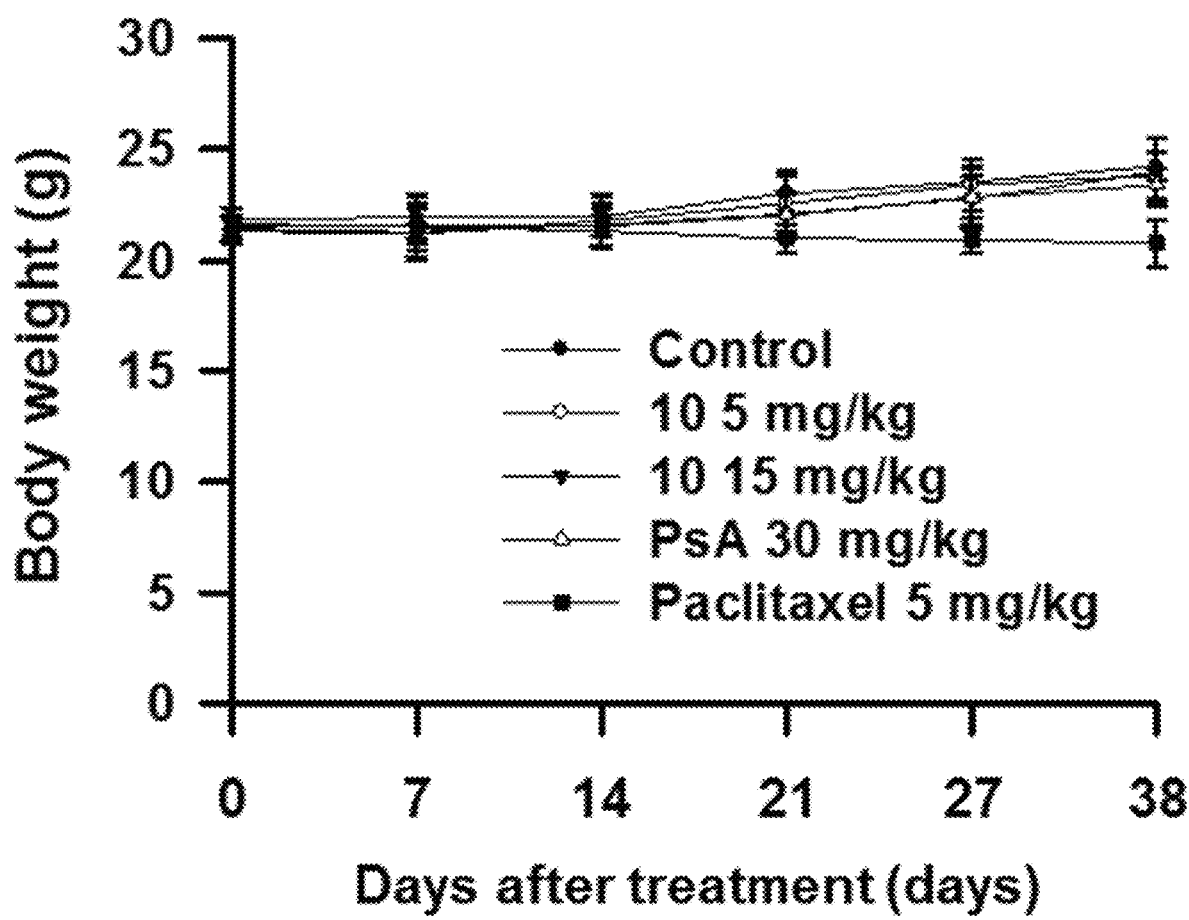
Figure 8D:
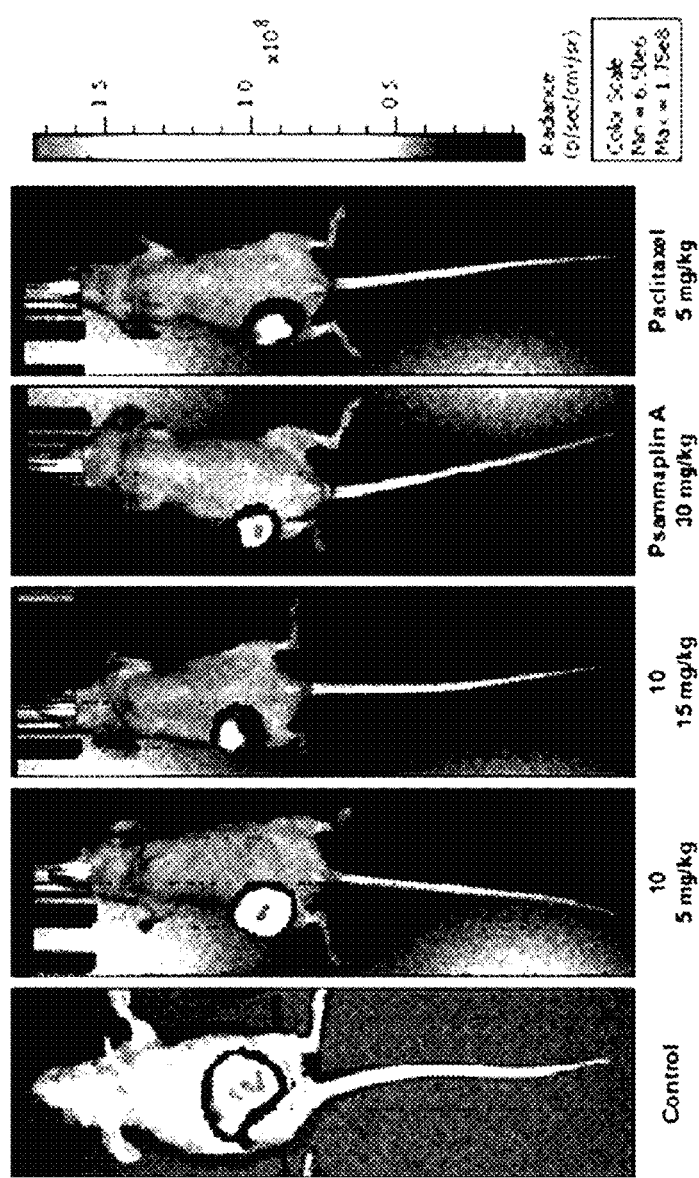

Breast cancer cells were injected into fat pads of nude BALB/c mice (8-week-old, female). When the tumor size reached about 200 mm$^3$, the compound was injected intraperitoneally three times a week. The tumor volume was calculated by the following equation: [volume (mg)=(L× W2)/2] and illustrated in FIG. 8A. 38 days after administration began, the mice were sacrificed and tumors were extracted, and the weights thereof were measured and illustrated in FIG. 8B. The body weights of the mice measured during the experiment are illustrated in FIG. 8C. Mice at the end of the experiment were photographed using IVIS (PerkinElmer) and the tumor size is indirectly shown in FIG. 8D.

As illustrated in FIGS. 8A to 8D, it was confirmed that, in the groups administered compound 2, tumor volume was remarkably reduced compared to the control, and tumor weight was also remarkably reduced compared to the control, a psammaplin A (PsA)-administered group, and a paclitaxel-administered group, and the body weights of the mice were not affected thereby, and thus such reductions are not due to the toxicity of the compound.

Example 9. Effect of Suppressing Breast Cancer Metastasis

The effect of suppressing the metastasis of breast tumors was examined using an animal model.

Figure 9:
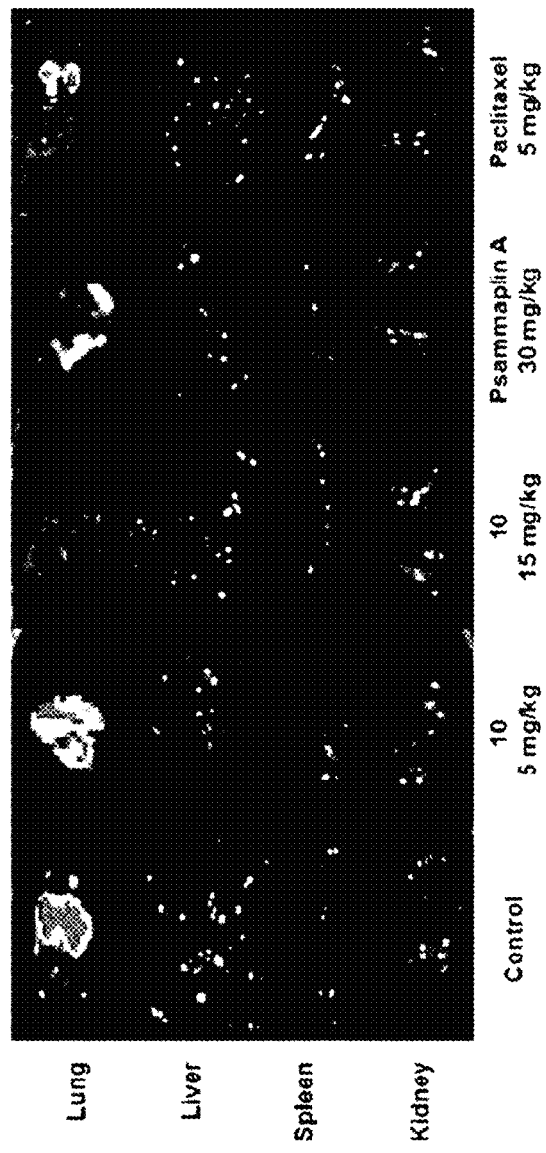
FIG. 9 illustrates results confirming the extent of metastasis of breast cancer cells to each of the lungs, liver, spleen, and kidneys in mice treated with compound 2 (5 mg/kg, 15 mg/kg).

Organs such as the lungs, liver, spleen, and kidneys were extracted from the animal model of Example 8, and the degrees of cancer metastasis in the control and the administered groups were indirectly photographed using IVIS (PerkinElmer) and are illustrated in FIG. 9.

As illustrated in FIG. 9, it was confirmed that the degree of metastasis to each organ was significantly reduced in the compound 2-administered groups, and particularly, the degree of metastasis to the lungs was greatly reduced.

Example 10. Confirmation of Expression of Cancer Metastasis Markers in Tumor Tissues To verify that compound 2 is involved in the regulation of key factors such as H3K79me2, E-cadherin, and vimentin in vivo, the effect of compound 2 on the key factors in tumor tissues was analyzed using the following method.

Figure 10A:
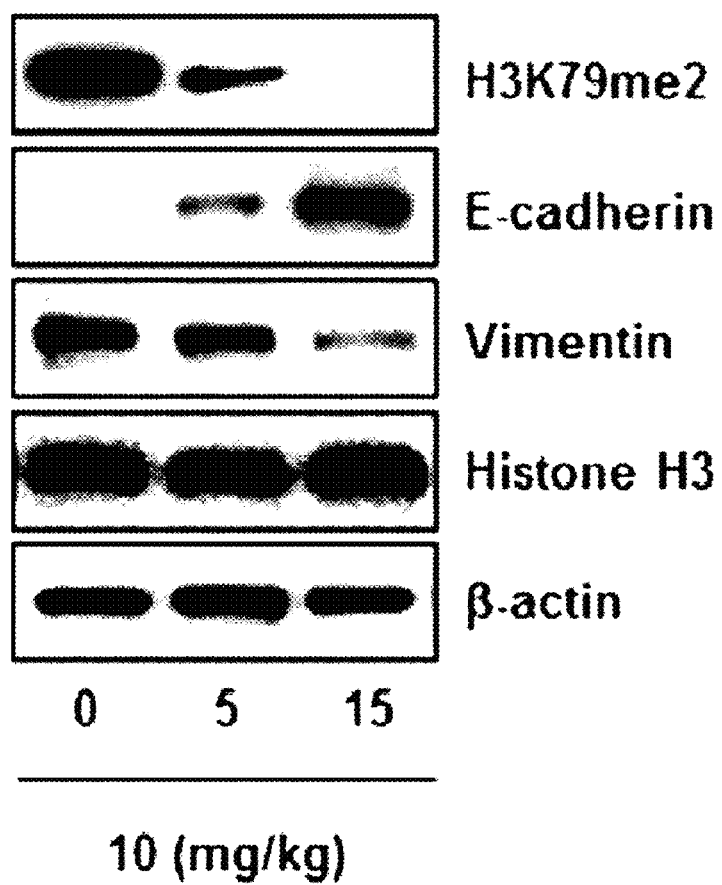
FIGS. 10A and 10B illustrate results confirming the degree of histone methylation and metastasis markers in breast tumors extracted from mice treated with compound 2 (10 mg/kg).

The triple-negative breast cancer cell line MDA-MB-231 was spread at a concentration of 2×10$^6$ cells/well on a DMEM medium containing 10% FBS in a 6-well plate, cultured at 37° C. for 24 hours under a 5% CO$_2$ condition, and then washed twice with phosphate-buffered saline (PBS). Attached cells were recovered and washed twice with PBS, and then boiling 2× sample loading buffer (250 mM Tris-HCl (pH 6.8), 4% SDS, 10% glycerol, 0.006% bromophenol blue, 2% β-mercaptoethanol, 50 mM sodium fluoride, and 5 mM sodium orthovanadate) was added thereto to disrupt the cells and the cells were left at 100° C. for 10 minutes. After cooling, the cells were stored at 20° C. and lysed at 37° C. immediately before use in protein quantification and electrophoresis. 10 µg of proteins were electrophoresed at 100 V for 2 hours using a 12% SDS-polyacrylamide gel (#456-1036, Bio-Rad, Hercules, Calif.). The separated proteins were transferred to a PVDF membrane (ISEQ15150, Millipore, Bedford, Mass.) at 100 V for 1 hour, and a blocking buffer (5% non-fat dry milk in TBS containing 0.1% Tween-20 (TBST)) was injected thereinto to culture the proteins at room temperature for 1 hour. After washing three times with TBST for 5 minutes, the corresponding single antibody was diluted with 5% non-fat dry milk in TBST and allowed to react with the membrane at 4° C. for 18 hours. The membrane [ISEQ 1S150, Millipore, Bedford, Mass.] was washed three times with TBST for 10 minutes, and then horseradish peroxidase (HRP)-conjugated secondary antibodies were diluted with 2.5% non-fat dry milk in TBST at a ratio of 1:2,000 and allowed to react with the membrane at room temperature for 2 hours. After washing three times with TBST for 10 minutes, the reaction product was treated with a chemiluminescent reagent (Lab-Frontier, Suwon, Korea) to confirm the protein expression levels of H3K79me2, E-cadherin, vimentin, histone H3, and β-actin using LAS-4000 (Fuji Film Corp., Japan), and the protein expression levels are illustrated in FIG. 10A. These were quantified using ImageJ software and are illustrated in FIG. 10B.

Figure 10B:
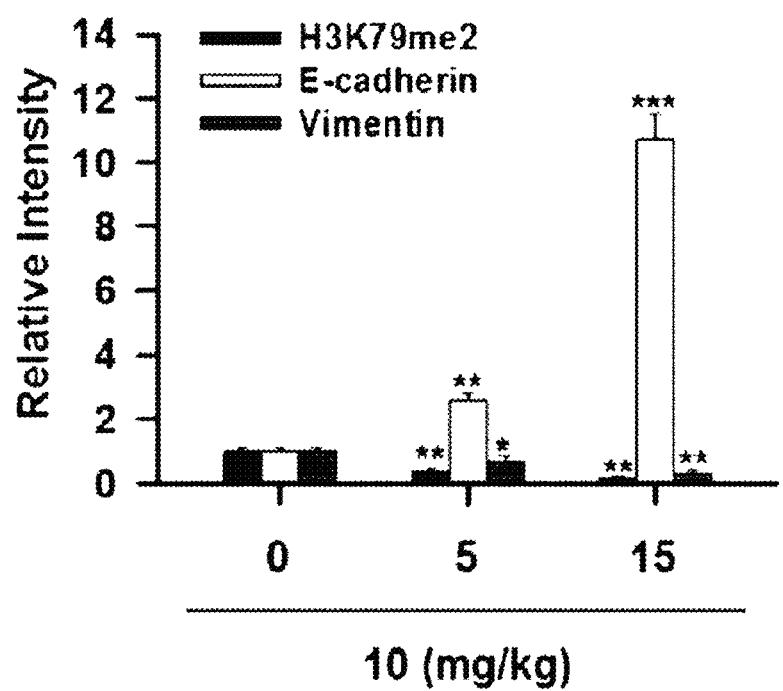

As illustrated in FIGS. 10A and 10B, it was confirmed that, in breast tumors extracted from mice treated with compound 2 (10 mg/kg), histone methylation and vimentin were reduced in a concentration-dependent manner, and E-cadherin was increased in a concentration-dependent manner.

Example 11. Immunohistological Confirmation of Cancer Metastasis Markers in Tumor Tissues 38 days after start of administration to the animal model, the mice were sacrificed and tumors were extracted to make paraffin blocks, and then changes in biomarkers related to carcinogenesis, such as Ki67, H3K79me2, E-cadherin, and vimentin, were investigated using an immunohistological method.

Figure 11:
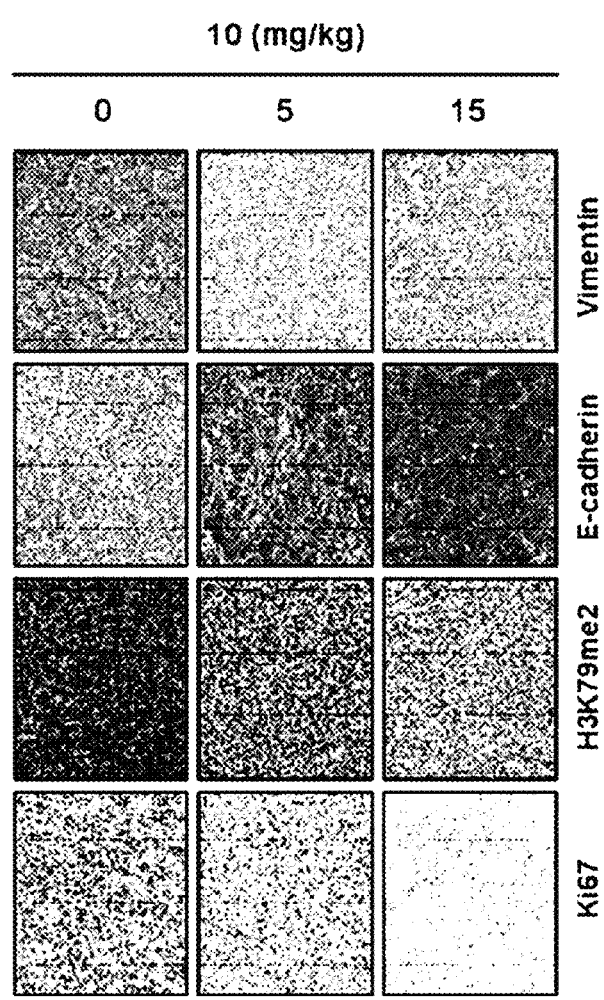
FIG. 11 illustrates results confirming protein expression in breast tumor tissue through immunostaining.

As illustrated in FIG. 11, it was confirmed that, as in the results of Example 10, histone methylation and vimentin were reduced in a concentration-dependent manner, and E-cadherin was increased in a concentration-dependent manner.

PREPARATION EXAMPLES

Preparation Example 1. Preparation of Powders

| | |
|---|---|
| Seleno-psammaplin A | 200 mg |
| Lactose | 100 mg |
| Talc | 10 mg |

The above ingredients are mixed and airtight packages are filled therewith, thereby completing the preparation of powders.

Preparation Example 2. Preparation of Tablets

| Seleno-psammaplin A | 200 mg |
|---|---|
| Corn starch | 100 mg |
| Lactose | 100 mg |
| Magnesium stearate | 2 mg |

The above ingredients were mixed, and then tablets are prepared according to a general method of preparing tablets.

Preparation Example 3. Preparation of Capsules

| Seleno-psammaplin A | 200 mg |
|---|---|
| Crystalline cellulose | 3 mg |
| Lactose | 14.8 mg |
| Magnesium stearate | 0.2 mg |

The above ingredients were mixed, and gelatin capsules are filled therewith according to a general method of preparing capsules, thereby completing the preparation of capsules.

Preparation Example 4. Preparation of Injections

| Seleno-psammaplin A | 200 mg |
|---|---|
| Mannitol | 180 mg |
| Injectable sterile distilled water | 2974 mg |
| $Na_2HPO_4 \cdot 12H_2O$ | 26 mg |

Ampoules are prepared according to a general method of preparing an injection such that the above ingredients are contained in a single ampoule (2 ml).

Preparation Example 5. Preparation of Liquids

| Seleno-psammaplin A | 200 mg |
|---|---|
| Isomerized sugar | 10 g |
| Mannitol | 5 g |
| Purified water | appropriate amount |

Each ingredient are added to and dissolved in purified water according to a general method of preparing a liquid, a lemon flavor are added in an appropriate amount, the above ingredients are mixed, purified water is added thereto such that a total amount of the resulting solution is adjusted to 100 ml, and a brown bottle is filled therewith, thereby completing the preparation of liquids.

Taken together, the inventors of the present invention confirmed that selenopsammaplin A and derivatives thereof exhibited not only very high anticancer activity against breast cancer, liver cancer, and gastric cancer but also a very strong effect of suppressing metastasis.

Therefore, the selenopsammaplin A and derivatives thereof of the present invention are expected to be used as a preventive or therapeutic agent for breast cancer and an inhibitor of breast cancer metastasis.

The foregoing description of the present invention is provided for illustrative purposes, and it will be understood by those of ordinary skill in the art to which the present invention pertains that the invention may be easily modified into many different forms without departing from the technical spirit or essential characteristics of the present invention. It is therefore to be understood that the above-described embodiments are illustrative in all aspects and not restrictive.

INDUSTRIAL APPLICABILITY

According to the present invention, it has been confirmed that, as a result of research on psammaplin A-related structural activity, a novel compound selenopsammaplin A, the disulfide moiety of which is substituted with diselenide, and derivatives thereof exhibit excellent anticancer activity against breast cancer, liver cancer, and gastric cancer cells, and exhibit not only a superior effect of suppressing the growth of breast cancer to that of existing psammaplin A but also an excellent effect of suppressing the metastasis of breast cancer cells, and the selenopsammaplin A and derivatives thereof can be effectively used as a pharmaceutical composition for preventing and treating breast cancer, liver cancer, and gastric cancer, and suppressing breast cancer metastasis, thus being industrially applicable.

The invention claimed is:

1. A method of preventing or treating cancer selected from the group consisting of breast cancer, liver cancer, and gastric cancer, comprising administering to an individual a pharmaceutical composition comprising an effective amount of selenopsammaplin A or a derivative thereof represented by Formula 1, or a pharmaceutically acceptable salt thereof:

[Formula 1]

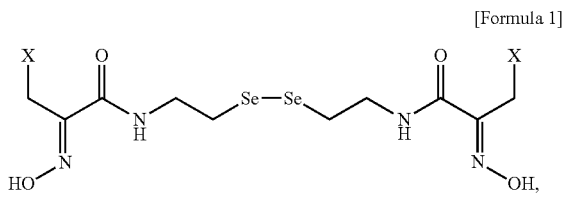

wherein X is hydrogen, a $C_{1-5}$ alkyl,

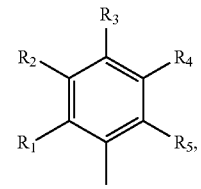

1-naphthyl, 2-naphthyl, or 9-anthracenyl, $R_1$ to $R_5$ are each independently selected from the group consisting of hydrogen, nitro, a halogen, cyano, hydroxy, dimethylamino, methylsulfonylamide, trifluoromethyl, a $C_{1-5}$ alkyl, a $C_{1-3}$ alkoxy, vinyl, aryl, phenoxy, and benzoxy;

$R_3$ and $R_4$ may be linked to form a ring represented by

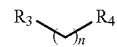

wherein n is an integer of 1, 2 or 3; and
where any of $R_1$ to $R_5$ is phenoxy or benzoxy, the aromatic ring may be substituted with a $C_{1-3}$ alkyl, a $C_{1-3}$ alkoxy, a halogen, trifluoromethyl, or t-butyl.

2. The method of claim 1, wherein the cancer is breast cancer.

3. The method of claim 1, wherein X is 2-naphthyl, or

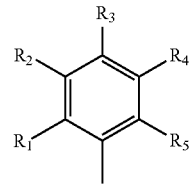

wherein $R_1$, $R_2$ and $R_5$ are each independently hydrogen, $R_3$ is hydrogen, hydroxy, ethoxy, t-butyl, fluoro, chloro, bromo, nitro or benzoxy, and $R_4$ is hydrogen, bromo, chloro or fluoro.

4. The method of claim 1, wherein selenopsammaplin A or a derivative thereof represented by Formula 1 is selected from the group consisting of:
   (2E,2'E)-N,N'(diselenediylbis(ethane-2,1-diyl))bis(3-(3-bromo-4-hydroxyphenyl)-2-(hydroxyimino)propanamide);
   (2E,2'E)-N,N'(diselenediylbis(ethane-2,1-diyl))bis(3-(3-chloro-4-hydroxyphenyl)-2-(hydroxyimino)propanamide);
   (2E,2'E)-N,N'(diselenediylbis(ethane-2,1-diyl))bis(3-(3-fluoro-4-hydroxyphenyl)-2-(hydroxyimino)propanamide);
   (2E,2'E)-N,N'(diselenediylbis(ethane-2,1-diyl))bis(2-(hydroxyimino)-3-phenylpropanamide);
   (2E,2'E)-N,N'(diselenediylbis(ethane-2,1-diyl))bis(3-(4-fluorophenyl)-2-(hydroxyimino)propanamide);
   (2E,2'E)-N,N'(diselenediylbis(ethane-2,1-diyl))bis(3-(4-chlorophenyl)-2-(hydroxyimino)propanamide);
   (2E,2'E)-N,N'(diselenediylbis(ethane-2,1-diyl))bis(3-(4-bromophenyl)-2-(hydroxyimino)propanamide);
   (2E,2'E)-N,N'(diselenediylbis(ethane-2,1-diyl))bis(3-(3,4-difluorophenyl)-2-(hydroxyimino)propanamide);
   (2E,2'E)-N,N'(diselenediylbis(ethane-2,1-diyl))bis(3,4-dichlorophenyl)-2-(hydroxyimino)propanamide);
   (2E,2'E)-N,N'(diselenediylbis(ethane-2,1-diyl))bis(3-(4-ethoxyphenyl)-2-(hydroxyimino)propanamide);
   (2E,2'E)-N,N'(diselenediylbis(ethane-2,1-diyl))bis(3-(4-benzyloxy)phenyl)-2-(hydroxyimino)propanamide);
   (2E,2'E)-N,N'(diselenediylbis(ethane-2,1-diyl))bis(2-(hydroxyimino)-3-(4-nitrophenyl)propanamide);
   (2E,2'E)-N,N'(diselenediylbis(ethane-2,1-diyl))bis(3-(4-tert-butyl)phenyl)-2-(hydroxyimino)propanamide); and
   (2E,2'E)-N,N'(diselenediylbis(ethane-2,1-diyl))bis(2-(hydroxyimino)-3-(naphthalene-2-yl)propanamide).

5. The method of claim 1, wherein the breast cancer is triple-negative breast cancer.

6. The method of claim 1, wherein the composition suppresses DOT1L activity.

7. A method of suppressing breast cancer metastasis, comprising administering to an individual a pharmaceutical composition comprising an effective amount of selenopsammaplin A or a derivative thereof represented by Formula 1, or a pharmaceutically acceptable salt thereof:

[Formula 1]

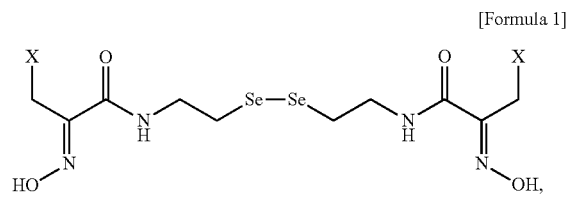

wherein X is hydrogen, a $C_{1-5}$ alkyl,

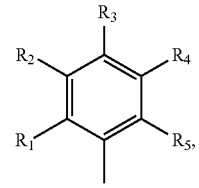

1-naphthyl, 2-naphthyl, or 9-anthracenyl;
   $R_1$ to $R_5$ are each independently selected from the group consisting of hydrogen, nitro, a halogen, cyano, hydroxy, dimethylamino, methylsulfonylamide, trifluoromethyl, a $C_{1-5}$ alkyl, a $C_{1-3}$ alkoxy, vinyl, aryl, phenoxy, and benzoxy;
   $R_3$ and $R_4$ may be linked to form a ring represented by

wherein n is an integer of 1, 2 or 3; and
   where any of $R_1$ to $R_5$ is phenoxy or benzoxy, the aromatic ring may be substituted with a $C_{1-3}$ alkyl, a $C_{1-3}$ alkoxy, a halogen, trifluoromethyl, or t-butyl.

8. The method of claim 7, wherein the breast cancer is triple-negative breast cancer.

9. The method of claim 7, wherein the composition has an effect of suppressing the growth, invasion, and migration of cancer cells.

10. The method of claim 7, wherein X is 2-naphthyl, or

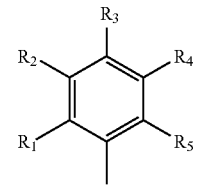

wherein $R_1$, $R_2$ and $R_5$ are each independently hydrogen, $R_3$ is hydrogen, hydroxy, ethoxy, t-butyl, fluoro, chloro, bromo, nitro or benzoxy, and $R_4$ is hydrogen, bromo, chloro or fluoro.

11. The method of claim 7, wherein selenopsammaplin A or a derivative thereof represented by Formula 1 is selected from the group consisting of:
   (2E,2'E)-N,N'(diselenediylbis(ethane-2,1-diyl))bis(3-(3-bromo-4-hydroxyphenyl)-2-(hydroxyimino)propanamide);
   (2E,2'E)-N,N'(diselenediylbis(ethane-2,1-diyl))bis(3-(3-chloro-4-hydroxyphenyl)-2-(hydroxyimino)propanamide);

(2E,2'E)-N,N'(diselenediylbis(ethane-2,1-diyl))bis(3-(3-fluoro-4-hydroxyphenyl)-2-(hydroxyimino)propanamide);

(2E,2'E)-N,N'(diselenediylbis(ethane-2,1-diyl))bis(2-(hydroxyimino)-3-phenylpropanamide);

(2E,2'E)-N,N'(diselenediylbis(ethane-2,1-diyl))bis(3-(4-fluorophenyl)-2-(hydroxyimino)propanamide);

(2E,2'E)-N,N-(diselenediylbis(ethane-2,1-diyl))bis(3-(4-chlorophenyl)-2-(hydroxyimino)propanamide);

(2E,2'E)-N,N-(diselenediylbis(ethane-2,1-diyl))bis(3-(4-bromophenyl)-2-(hydroxyimino)propanamide);

(2E,2'E)-N,N-(diselenediylbis(ethane-2,1-diyl))bis(3-(3,4-difluorophenyl)-2-(hydroxyimino)propanamide);

(2E,2'E)-N,N-(diselenediylbis(ethane-2,1-diyl))bis(3,4-dichlorophenyl)-2-(hydroxyimino)propanamide);

(2E,2'E)-N,N-(diselenediylbis(ethane-2,1-diyl))bis(3-(4-ethoxyphenyl)-2-(hydroxyimino)propanamide);

(2E,2'E)-N,N-(diselenediylbis(ethane-2,1-diyl))bis(3-(4-benzyloxy)phenyl)-2-(hydroxyimino)propanamide);

(2E,2'E)-N,N-(diselenediylbis(ethane-2,1-diyl))bis(2-(hydroxyimino)-3-(4-nitrophenyl)propanamide);

(2E,2'E)-N,N-(diselenediylbis(ethane-2,1-diyl))bis(3-(4-tert-butyl)phenyl)-2-(hydroxyimino)propanamide); and (2E,2'E)-N,N-(diselenediylbis(ethane-2,1-diyl))bis(2-(hydroxyimino)-3-(naphthalene-2-yl)propanamide).

\* \* \* \* \*